(12) United States Patent
Efrati et al.

(10) Patent No.: US 10,780,238 B2
(45) Date of Patent: *Sep. 22, 2020

(54) METHOD OF DETECTING ENDOTRACHEAL TUBE MISPLACEMENT

(71) Applicant: Hospitech Respiration Ltd., Petach-Tikva (IL)

(72) Inventors: Shai Efrati, Rechovot (IL); Israel Deutsch, Petach-Tikva (IL)

(73) Assignee: Hospitech Respiration Ltd., Kfar-Saba (IL)

(*) Notice: Subject to any disclaimer, the term of this patent is extended or adjusted under 35 U.S.C. 154(b) by 1318 days.

This patent is subject to a terminal disclaimer.

(21) Appl. No.: 14/684,385

(22) Filed: Apr. 12, 2015

(65) Prior Publication Data
US 2015/0209532 A1   Jul. 30, 2015

Related U.S. Application Data

(63) Continuation of application No. 12/984,673, filed on Jan. 5, 2011, now Pat. No. 9,004,069, which is a
(Continued)

(51) Int. Cl.
*A61M 16/00* (2006.01)
*A61M 16/04* (2006.01)

(52) U.S. Cl.
CPC .... *A61M 16/0051* (2013.01); *A61M 16/0003* (2014.02); *A61M 16/021* (2017.08);
(Continued)

(58) Field of Classification Search
CPC .............. A61M 16/00; A61M 16/0003; A61M 16/0051; A61M 16/021; A61M 16/022;
(Continued)

(56) References Cited

U.S. PATENT DOCUMENTS 3,504,676 A   6/1970   Lomholt
3,794,036 A   2/1974   Carroll
(Continued)

FOREIGN PATENT DOCUMENTS

CN   1535167   10/2004
DE   4009468   9/1991
(Continued)

OTHER PUBLICATIONS

Notice of Reexamination dated Aug. 12, 2015 From the Patent Reexamination Board of State Intellectual Property Office of the People's Republic of China Re. Application No. 200680052386.4 and Its Translation Into English.
(Continued)

*Primary Examiner* — Colin W Stuart

(57) ABSTRACT

In an alerting and controlling system, there is a measuring device and a controller. The measuring device is connectable to an endotracheal tube associated with a cuff inflatable below the vocal cords of a subject, for measuring at least one measure being indicative of the presence of leakage of secretions from above the cuff to the lungs of the subject. The controller adjusts inflation of the cuff responsively to the level of the at least one measure such as to reduce or prevent leakage of secretions from above the cuff to the lungs, and alerts that the endotracheal tube is malpositioned in the airway of the subject if an inflation pressure of the cuff exceeds a predetermined threshold.

20 Claims, 20 Drawing Sheets

Related U.S. Application Data continuation of application No. 11/990,694, filed as application No. PCT/IL2006/000974 on Aug. 21, 2006, now Pat. No. 8,424,529.

(60) Provisional application No. 60/754,191, filed on Dec. 28, 2005, provisional application No. 60/721,965, filed on Sep. 30, 2005, provisional application No. 60/710,678, filed on Aug. 24, 2005.

(52) U.S. Cl.
CPC ........ *A61M 16/022* (2017.08); *A61M 16/024* (2017.08); *A61M 16/04* (2013.01); *A61M 16/044* (2013.01); *A61M 16/0434* (2013.01); *A61M 16/0463* (2013.01); *A61M 2016/0027* (2013.01); *A61M 2016/0413* (2013.01); *A61M 2205/15* (2013.01); *A61M 2205/3303* (2013.01); *A61M 2205/3306* (2013.01); *A61M 2205/3317* (2013.01); *A61M 2205/3327* (2013.01); *A61M 2205/3334* (2013.01); *A61M 2205/3344* (2013.01); *A61M 2205/3375* (2013.01); *A61M 2205/702* (2013.01); *A61M 2210/0618* (2013.01); *A61M 2230/432* (2013.01)

(58) Field of Classification Search
CPC .. A61M 16/024; A61M 16/026; A61M 16/04; A61M 16/0402; A61M 16/0411; A61M 16/0434; A61M 16/044; A61M 16/0463; A61M 2016/0413; A61M 2016/103; A61M 2205/33; A61M 2205/3327; A61M 2205/3331; A61M 2205/3344; A61M 2230/432; A61M 2205/15
See application file for complete search history.

(56) References Cited

U.S. PATENT DOCUMENTS

| | | | |
|---|---|---|---|
| 4,159,722 A | 7/1979 | Walker | |
| 4,198,970 A | 4/1980 | Luomanen | |
| 4,305,392 A | 12/1981 | Chester | |
| 4,383,534 A | 5/1983 | Peters | |
| 4,501,273 A | 2/1985 | McGinnis | |
| 4,607,635 A | 8/1986 | Heyden | |
| 4,632,108 A | 12/1986 | Geil | |
| 4,691,701 A | 9/1987 | Williams | |
| 4,770,170 A | 9/1988 | Sato et al. | |
| 4,790,327 A * | 12/1988 | Despotis | A61M 16/0488 128/205.23 |
| 4,813,431 A | 3/1989 | Brown | |
| 4,825,862 A | 5/1989 | Sato et al. | |
| 4,850,371 A | 7/1989 | Broadhurst et al. | |
| 4,924,862 A | 5/1990 | Levinson | |
| 4,994,117 A | 2/1991 | Fehder | |
| 5,067,497 A | 11/1991 | Greear et al. | |
| 5,095,896 A | 3/1992 | Omoigui | |
| 5,193,544 A | 3/1993 | Jaffe | |
| 5,197,464 A | 3/1993 | Babb et al. | |
| 5,235,973 A | 8/1993 | Levinson | |
| 5,251,619 A | 10/1993 | Lee | |
| 5,264,697 A | 11/1993 | Nakagawa et al. | |
| 5,285,778 A | 2/1994 | Mackin | |
| 5,291,879 A | 3/1994 | Babb et al. | |
| 5,354,267 A | 10/1994 | Niermann et al. | |
| 5,360,003 A | 11/1994 | Capistrano | |
| 5,360,414 A | 11/1994 | Yarger | |
| 5,361,753 A | 11/1994 | Pothmann et al. | |
| 5,400,771 A * | 3/1995 | Pirak | A61B 1/042 600/109 |
| 5,445,144 A | 8/1995 | Wodicka et al. | |
| 5,445,161 A | 8/1995 | Huang | |
| 5,499,625 A | 3/1996 | Frass et al. | |
| 5,579,762 A | 12/1996 | Lee | |
| 5,582,166 A | 12/1996 | Lee | |
| 5,582,167 A | 12/1996 | Joseph | |
| 5,622,182 A | 4/1997 | Jaffe | |
| 5,669,380 A | 9/1997 | Garry et al. | |
| 5,697,365 A | 12/1997 | Pell | |
| 5,752,921 A | 5/1998 | Orr | |
| 5,765,559 A | 6/1998 | Kim | |
| 5,785,051 A | 7/1998 | Lipscher et al. | |
| 5,791,341 A | 8/1998 | Bullard | |
| 5,803,078 A | 9/1998 | Brauner | |
| 5,819,723 A | 10/1998 | Joseph | |
| 5,819,727 A * | 10/1998 | Linder | A61M 16/0488 128/200.26 |
| 5,919,183 A | 7/1999 | Field | |
| 5,937,861 A | 8/1999 | Augustine | |
| 6,059,732 A | 5/2000 | Orr et al. | |
| 6,062,223 A | 5/2000 | Palazzo et al. | |
| 6,071,237 A | 6/2000 | Weil et al. | |
| 6,098,617 A | 8/2000 | Connell | |
| 6,135,105 A | 10/2000 | Lampotang et al. | |
| 6,315,739 B1 | 11/2001 | Merilainen et al. | |
| 6,450,164 B1 | 9/2002 | Banner et al. | |
| 6,474,332 B2 | 11/2002 | Arndt | |
| 6,550,475 B1 | 4/2003 | Oldfield | |
| 6,568,388 B2 | 5/2003 | Christopher | |
| 6,568,393 B2 | 5/2003 | Christopher | |
| 6,571,796 B2 | 6/2003 | Banner et al. | |
| 6,843,250 B2 | 1/2005 | Efrati | |
| 7,036,501 B2 | 5/2006 | Wall | |
| 7,171,962 B1 | 2/2007 | Bloem | |
| 7,278,420 B2 | 10/2007 | Ganesh et al. | |
| 7,360,541 B2 | 4/2008 | Dhuper et al. | |
| 7,503,328 B2 | 3/2009 | Kolobow et al. | |
| 7,954,488 B2 | 6/2011 | Munn | |
| 8,424,529 B2 | 4/2013 | Efrati et al. | |
| 9,004,069 B2 * | 4/2015 | Efrati | A61M 16/044 128/207.15 |
| 2002/0014238 A1 | 2/2002 | Kotmel | |
| 2002/0078962 A1 | 6/2002 | Nash et al. | |
| 2003/0051733 A1 | 3/2003 | Kotmel et al. | |
| 2003/0145860 A1 | 8/2003 | Johnson | |
| 2003/0172925 A1 | 9/2003 | Zocca et al. | |
| 2004/0123867 A1 | 7/2004 | Efrati | |
| 2004/0129272 A1 | 7/2004 | Ganesh et al. | |
| 2005/0039754 A1 | 2/2005 | Simon | |
| 2005/0045180 A1 | 3/2005 | Heinonen | |
| 2005/0279354 A1 | 12/2005 | Deutsch et al. | |
| 2006/0081255 A1 * | 4/2006 | Miller | A61B 8/0833 128/207.14 |
| 2007/0044807 A1 | 3/2007 | Madsen et al. | |
| 2007/0137651 A1 | 6/2007 | Glassenberg et al. | |
| 2008/0000481 A1 | 1/2008 | Ganesh et al. | |
| 2009/0013995 A1 | 1/2009 | Williams | |
| 2009/0038620 A1 | 2/2009 | Efrati | |
| 2009/0229605 A1 | 9/2009 | Efrati et al. | |
| 2011/0100373 A1 | 5/2011 | Efrati et al. | |
| 2012/0000471 A1 | 1/2012 | Harrington et al. | |
| 2017/0113011 A1 | 4/2017 | Efrati | |

FOREIGN PATENT DOCUMENTS

| | | |
|---|---|---|
| DE | 19734821 | 2/1999 |
| EP | 0347101 | 12/1989 |
| EP | 0640357 | 3/1995 |
| EP | 0728493 | 8/1996 |
| EP | 1418969 | 5/2004 |
| GB | 1414344 | 11/1975 |
| HU | 179929 | 5/1982 |
| HU | 206458 | 3/1992 |
| HU | P0003171 | 2/2001 |
| HU | P0104580 | 12/2002 |
| IL | 142228 | 4/2007 |
| JP | 06-504454 | 5/1994 |
| JP | 09-313609 | 9/1997 |
| JP | 10-165505 | 6/1998 |
| JP | 10-337326 | 12/1998 |
| JP | 10-504733 | 12/1998 |

(56) References Cited

FOREIGN PATENT DOCUMENTS

| JP | 2001-513372 | 9/2001 |
|---|---|---|
| JP | 2002-210014 | 7/2002 |
| JP | 2004-136118 | 5/2004 |
| JP | 2004-528887 | 9/2004 |
| WO | WO 92/07602 | 5/1992 |
| WO | WO 95/33506 | 12/1995 |
| WO | WO 99/029358 | 6/1999 |
| WO | WO 00/048510 | 8/2000 |
| WO | WO 02/076279 | 10/2002 |
| WO | WO 03/101516 | 12/2003 |
| WO | WO 2004/030527 | 4/2004 |
| WO | WO 2005/112796 | 12/2005 |
| WO | WO 2005/118039 | 12/2005 |
| WO | WO 2007/023492 | 3/2007 |
| WO | WO 2007/066332 | 6/2007 |

OTHER PUBLICATIONS

Communication Pursuant to Article 93(3) EPC dated Jan. 30, 2017 From the European Patent Office Re. Application No. 06780425.2. (4 Pages).
Communication Relating to the Results of the Partial International Search dated Jan. 25, 2007 From the International Searching Authority Re.: Application No. PCT/IL2006/000974.
Communication Relating to the Results of the Partial International Search dated Mar. 27, 2007 From the International Searching Authority Re.: Application No. PCT/IL2006/001401.
International Preliminary Report on Patentability dated May 6, 2008 From the International Preliminary Examining Authority Re.: Application No. PCT/IL2006/001401.
International Preliminary Report on Patentability dated Dec. 19, 2007 From the International Preliminary Examining Authority Re.: Application No. PCT/IL2006/000974.
International Preliminary Report on Patentability dated Mar. 27, 2008 From the International Preliminary Examining Authority Re.: Application No. PCT/IL2006/001401.
Applicant-Initiated Interview Summary dated Sep. 12, 2013 From the US Patent and Trademark Office Re. U.S. Appl. No. 12/085,909.
Communication Pursuant to Article 94(3) and Rule 71(1) EPC dated Mar. 19, 2013 From the European Patent Office Re. Application No. 06821620.9.
Communication Pursuant to Article 94(3) EPC dated Aug. 2, 2011 From the European Patent Office Re. Application No. 06821620.9.
Communication Pursuant to Article 94(3) EPC dated Aug. 7, 2009 From the European Patent Office Re.: Application No. 02707077.0.
Communication Pursuant to Article 94(3) EPC dated Dec. 13, 2011 From the European Patent Office Re. Application No. 06821620.9.
Communication Under Rule 71(3) EPC dated Oct. 9, 2013 From the European Patent Office Re. Application No. 06821620.9.
Corrected Written Opinion dated Jan. 6, 2010 From the Intellectual Property Office of Singapore Issued by the Danish Patent and Trademark Office Re.: Application No. SG200804735-9.
Examination Report dated Dec. 4, 2009 From the Intellectual Property Office of New Zealand Re.: Application No. 566767.
Examination Report dated Oct. 8, 2010 From the Intellectual Property Office of New Zealand Re. Application No. 588268.
Examination Report dated Sep. 13, 2007 From the Government of India, Patent Office Re.: Application No. 982/MUMNP/2003.
Examination Report dated Oct. 20, 2010 From the Intellectual Property Office of New Zealand Re.: Application No. 566767.
Examination Report dated Dec. 21, 2009 From the Intellectual Property Office of New Zealand Re.: Application No. 569496.
Examination Report dated Oct. 22, 2013 From the Instituto Mexicano de la Propiedad Industrial Re. Application No. MX/a/2008/007080 and Its Translation Into English.
Examination Report dated Nov. 24, 2009 From the Intellectual Property Office of New Zealand Re.: Application No. 569496.
Examination Report dated Jun. 28, 2013 From the Instituto Mexicano de la Propiedad Industrial Re. Application No. MX/a/2008/002397 and Its Translation Into English.
Examiner's Report dated Feb. 20, 2012 From the Australian Government, IP Australia Re. Application 2006282737.
Examiner's Report dated Sep. 23, 2005 From the Australian Government, IP Australia Re.: Application No. 2002241229.
Examiner's Report dated Sep. 28, 2006 From the Australian Government, IP Australia Re.: Application No. 2002241229.
International Search Report dated May 2, 2003 From the International Searching Authority Re.: Application No. PCT/IL02/00230.
International Search Report dated May 11, 2007 From the International Searching Authority Re.: Application No. PCT/IL2006/000974.
International Search Report dated Aug. 14, 2007 From the International Searching Authority Re.: Application No. PCT/IL2006/001401.
Interview Summary dated Aug. 2, 2011 From the U.S. Appl. No. 11/990,694.
Justification dated Jan. 12, 2009 From the Polish Industrial Property Office Re.: Application No. P-373498 and Its Translation Into English.
Notice of Allowance and Fee(s) Due dated Sep. 9, 2004 From the US Patent and Trademark Office Re.: U.S. Appl. No. 10/471,777.
Notice of Allowance dated Oct. 10, 2012 From the US Patent and Trademark Office Re. U.S. Appl. No. 11/990,694.
Notice of Allowance dated Dec. 18, 2014 From the US Patent and Trademark Office Re. U.S. Appl. No. 12/984,673.
Notice of Reexamination dated Dec. 26, 2014 From the Patent Reexamination Board of State Intellectual Property Office of the People's Republic of China Re. Application No. 200680052386.4 and Its Translation Into English.
Office Action dated Oct. 6, 2011 From the Israel Patent Office Re. Application No. 189689 and Its Translation Into English.
Office Action dated Sep. 16, 2010 From the Hungarian Patent Office (HPO) Re. Application No. P0400315.
Office Action dated May 26, 2010 From the Israel Patent Office Re. Application No. 189689 and Its Translation Into English.
Office Action dated Jul. 27, 2010 From the Israel Patent Office Re. Application No. 192006 and Its Translation Into English.
Office Action dated Mar. 28, 2012 From the Israel Patent Office Re. Application No. 192006 and Its Translation Into English.
Office Action dated Jan. 30, 2014 From the Israel Patent Office Re. Application No. 189689 and Its Translation Into English.
Official Action dated May 3, 2011 From the US Patent and Trademark Office Re. U.S. Appl. No. 11/990,694.
Official Action dated Oct. 5, 2010 From the US Patent and Trademark Office Re. U.S. Appl. No. 11/990,694.
Official Action dated Oct. 9, 2014 From the US Patent and Trademark Office Re. U.S. Appl. No. 12/085,909.
Official Action dated Apr. 11, 2013 From the US Patent and Trademark Office Re. U.S. Appl. No. 12/984,673.
Official Action dated Oct. 11, 2011 From the US Patent and Trademark Office Re. U.S. Appl. No. 12/984,673.
Official Action dated Sep. 14, 2011 From the US Patent and Trademark Office Re. U.S. Appl. No. 12/085,909.
Official Action dated Apr. 16, 2015 From the US Patent and Trademark Office Re. U.S. Appl. No. 12/085,909.
Official Action dated Mar. 16, 2012 From the US Patent and Trademark Office Re. U.S. Appl. No. 12/085,909.
Official Action dated Dec. 17, 2013 From the US Patent and Trademark Office Re. U.S. Appl. No. 12/085,909.
Official Action dated Dec. 22, 2011 From the US Patent and Trademark Office Re. U.S. Appl. No. 11/990,694.
Official Action dated Jul. 23, 2012 From the US Patent and Trademark Office Re. U.S. Appl. No. 12/984,673.
Official Action dated Aug. 25, 2014 From the US Patent and Trademark Office Re. U.S. Appl. No. 12/984,673.
Official Action dated Oct. 25, 2012 From the US Patent and Trademark Office Re. U.S. Appl. No. 12/085,909.
Official Action dated Jun. 28, 2013 From the US Patent and Trademark Office Re. U.S. Appl. No. 12/085,909.

(56) References Cited

OTHER PUBLICATIONS

Decision to Grant dated Mar. 4, 2014 From the Japanese Patent Office Re. Application No. 2008-544000 and Its Translation Into English.
Patent Examination Report dated Aug. 1, 2013 From the Australian Government, IP Australia Re. Application No. 2006322905.
Patent Examination Report dated Jun. 21, 2012 From the Australian Government, IP Australia Re. Application No. 2006322905.
Patent Examination Report dated Oct. 23, 2012 From the Australian Government, IP Australia Re. Application No. 2006282737.
Requisition by the Examiner dated Apr. 4, 2013 From the Canadian Intellectual Property Office Re. Application No. 2,631,516.
Requisition by the Examiner dated Aug. 5, 2013 From the Canadian Intellectual Property Office Re. Application No. 2,619,687.
Requisition by the Examiner dated Nov. 21, 2013 From the Canadian Intellectual Property Office Re. Application No. 2,631,516.
Requisition by the Examiner dated Nov. 27, 2012 From the Canadian Intellectual Property Office Re. Application No. 2,619,687.
Search Report and Written Opinion dated Feb. 9, 2009 From the Intellectual Property Office of Singapore Issued by the Danish Patent and Trademark Office Re.: Application No. 200804735-9.
Search Report dated Nov. 7, 2008 From the Intellectual Property Office of Singapore Issued by the Australian Patent Office Re.: Application No. 200801440-9.
Summons to Attend Oral Proceedings Pursuant to Rule 115(1) EPC dated Oct. 11, 2012 From the European Patent Office Re. Application No. 06821620.9.
Supplementary European Search Report dated Jun. 4, 2009 From the European Patent Office Re.: Application No. EP 02707077.
Translation of Notice of the Reason for Rejection dated Jun. 17, 2013 From the Korean intellectual Property Office Re. Application No. 2008-7006807.
Translation of Decision on Rejection dated Apr. 2, 2013 From the State Intellectual Property Office of the People's Republic of China Re. Application No. 200680052386.4.
Translation of Notice of Reason for Rejection dated Sep. 21, 2012 From the Japanese Patent Office Re. Application No. 2008-544000.
Translation of Notice of Reason for Rejection dated Nov. 25, 2011 From the Japanese Patent Office Re. Application No. 2008-544000.
Translation of Notice of Reason for Rejection dated Jul. 26, 2011 From the Japanese Patent Office Re. Application No. 2008-527592.
Translation of Notice of the Reason for Rejection dated Nov. 8, 2012 From the Korean Intellectual Property Office Re. Application No. 2008-7006807.
Translation of Notification of Reasons for Refusal dated Mar. 25, 2008 From the Japanese Patent Office Re.: Application No. 2002-574801.
Translation of Office Action dated Dec. 3, 2012 From the State Intellectual Property Office of the People's Republic of China Re. Application No. 200680052386.4.
Translation of Office Action dated May 3, 2012 From the State Intellectual Property Office of the People's Republic of China Re. Application No. 201010552126.1.
Translation of Office Action dated Oct. 10, 2012 From the State Intellectual Property Office of the People's Republic of China Re. Application No. 201010552126.1.
Translation of Office Action dated Nov. 16, 2011 From the State Intellectua Property Office of the People's Republic of China Re. Application No. 200680039482.5.
Translation of Office Action dated Jan. 19, 2011 From the State Intellectual Property Office of the People's Republic of China Re. Application No. 200680052386.4.
Translation of Office Action dated Jun. 24, 2011 From the State Intellectual Property Office of the People's Republic of China Re. Application No. 201010552126.1.
Translation of Office Action dated May 25, 2010 From the State Intellectual Property Office of the People's Republic of China Re. Application No. 200680039482.5.
Translation of Office Action dated Mar. 28, 2012 From the State Intellectual Property Office of the People's Republic of China Re. Application No. 200680052386.4.
Translation of Reason for Rejection dated Jun. 28, 2013 From the Japanese Patent Office Re. Application No. 2008-544000.
Translation of the Essential Parts of the Official Letter dated Aug. 3, 2012 From the Patent Office of the Czech Republic Re. Application No. 2003-2785.
Translation of the Office Action dated Oct. 31, 2005 From the State Intellectual Property Office of the People's Republic of China Re.: Application No. 02801194.5.
Written Opinion dated Nov. 7, 2008 From the Intellectual Property Office of Singapore Issued by the Australian Patent Office Re.: Application No. 200801440-9.
Written Opinion dated Feb. 9, 2009 From the Intellectual Property Office of Singapore Issued by the Danish Patent and Trademark Office Re.: Application No. SG200804735-9.
Written Opinion dated May 11, 2007 From the International Searching Authority Re.: Application No. PCT/IL2006/000974.
Written Opinion dated Aug. 14, 2007 From the International Searching Authority Re.: Application No. PCT/IL2006/001401.
Written Opinion dated Jun. 19, 2009 From the Intellectual Property Office of Singapore Issued by the Australian Government, IP Australia Re.: Application No. SG 200801440-9.
Written Opinion dated Sep. 28, 2009 From the Intellectual Property Office of Singapore Issued by the Danish Patent and Trademark Office Re.: Application No. SG 200804735-9.
Efrati et al. "Optimization of Endotracheal Tube Cuff Filling by Continuous Upper Airway Carbon Dioxide Monitoring", Anesthesia & Analgesia, 101(4): 1081-1088, 2005.
Examination Report Under Sections 12 & 13 of the Patents Act, 1970 and the Patents Rules, 2003 dated Feb. 14, 2017 From the Government of India, Patent Office, Intellectual Property Building Re. Application No. 1425/CHENP/2008. (7 Pages).
Examination Report dated Mar. 15, 2016 From the Government of India, Patent Office, Intellectual Property Building Re. Application No. 05711/DELNP/2008.
Official Action dated Feb. 1, 2016 From the US Patent and Trademark Office Re. U.S. Appl. No. 12/085,909.
Office Action dated Apr. 21, 2016 From the State Intellectual Property Office of the People's Republic of China Re. Application No. 200680052386.4 and Its Translation Into English.
Hearing Notice dated Jul. 26, 2019 From the Government of India, Patent Office, Intellectual Property Building Re. Application No. 05711/DELNP/2008. (3 Pages).
Official Action dated Oct. 9, 2019 From the US Patent and Trademark Office Re. U.S. Appl. No. 15/398,773. (33 pages).
Final Official Action dated Jul. 17, 2020 from the US Patent and Trademark Office Re. U.S. Appl. No. 15/398,773. (18 pages).

* cited by examiner

METHOD OF DETECTING ENDOTRACHEAL TUBE MISPLACEMENT

RELATED APPLICATIONS

This application is a continuation of U.S. patent application Ser. No. 12/984,673 filed on Jan. 5, 2011, now U.S. Pat. No. 9,004,069, which is a continuation of U.S. patent application Ser. No. 11/990,694, filed on Feb. 20, 2008, now U.S. Pat. No. 8,424,529, which is a National Phase of PCT Patent Application No. PCT/IL2006/000974 having International Filing Date of Aug. 21, 2006, which claims the benefit of priority of U.S. Provisional Patent Application Nos. 60/754,191 filed on Dec. 28, 2005, 60/721,965 filed on Sep. 30, 2005, and 60/710,678 filed on Aug. 24, 2005. The contents of the above Applications are all incorporated herein by reference.

FIELD AND BACKGROUND OF THE INVENTION

The present invention relates to intubation and, more particularly, to a system and method for performing endotracheal intubation and adjusting endotracheal tube cuff filling.

In the medical treatment of patients requiring breathing assistance, it is common to insert an endotracheal tube into the trachea of the patient, by way of the mouth, nose or any other surgically created opening. One end of the endotracheal tube is connected to a ventilator which periodically forces air into the lungs through the tube. The inner end of the tube is typically provided with an inflatable cuff which is inflated by conventional means subsequently to the insertion of the tube into the trachea. The inflated cuff is supposed to provides a seal against the interior wall of the trachea.

In such cuffed endotracheal tubes, if the cuff is brought into contact with the inner wall of the trachea under too high pressure, normal blood flow in the mucosa is disturbed due to excess pressure for capillary vessels at the contact portion, resulting in tissue ischemia or inadequate blood flow. Prolonged ischemia can cause varying degrees of injury, such as erosion of the mucosa, destruction of the tracheal cartilage rings, or segmental tracheomalacia with dilation of the trachea. Even more dramatic is full thickness erosion which may result in perforation of the innominate artery anteriorly or perforation of the esophagus posteriorly. Patients requiring long term ventilatory support oftentimes developed late complications of tracheal stenosis, from mild to incapacitating obstruction.

On the other hand, if the cuff is brought into contact with the inner wall of the trachea under too low a pressure, the artificial respiration can be inhibited due to a leakage of anesthetic gas, oxygen or air. Furthermore, when the pressure is low, bodily secretions, mucous or other unwanted fluids can pass progressively between the inner surface of the trachea and the outer surface of the cuff. These secretions can pass from the trachea and enter the bronchi, potentially to cause lung infections.

It is therefore necessary to maintain the cuff contact pressure on the inner wall of the trachea at an appropriate level so as to prevent the leakage of air from between the inflated cuff and the tracheal wall during mechanical ventilation, while at the same time maintaining the necessary blood flow in the capillaries at the contact portion.

To prevent tissue damage caused by prolonged pressure from the cuff, the physician periodically deflates and re-inflates the cuff. However, this procedure is rarely done frequently enough or for a long enough period of time to allow adequate reperfusion of the tissue. Therefore, this procedure does not dependably prevent tracheal wall ischemia.

A variety of endotracheal tubes have been developed. For example, U.S. Pat. No. 4,159,722 discloses an improved pressure regulator for an inflatable cuff on an endotracheal tube which prevents relatively rapid pressure increases and permits relatively slow pressure increases. The pressure regulator provides a visual indication of the air pressure in the cuff.

U.S. Pat. No. 4,305,392 attempts to solve the problem of secretion leakage by suctioning. The endotracheal tube is combined with a suction device in a form of a chamber with suction ports for suctioning out fluids in the trachea above the cuff and for introducing medicinal fluids into the trachea.

U.S. Pat. No. 4,501,273 attempts to solve the problem of leakage by controlling the cuff. The pressure within the cuff automatically increases in proportion with the increases in pressure fed to the interior of the endotracheal tube, thereby preventing breakdown or leakage in the seal between the inflated cuff and the trachea wall.

U.S. Pat. No. 5,765,559 addresses the issue of constant static pressure exerted by the cuff on the tracheal wall which, during prolonged surgery, may result in tracheal stenosis. The proposed solution includes a cuffed endotracheal tube having a plurality of cuff rings, each being capable of inflating and deflating periodically such that when one or more of the cuff rings deflate the others remains inflated. This reduces damage to the tracheal wall due to constant pressure on fixed locations.

None of the above and other prior art technologies, however, monitor leakage at the contact area between the cuff and the tracheal inner wall.

A different approach is disclosed in International Patent Application, Publication No. WO 2002/076279 and U.S. Pat. No. 6,843,250 both filed by the Inventor of the present invention. In this approach, the concentration of carbon dioxide is monitored in the patient's airway between the cuff and the vocal cords. Based on the monitoring, the inflation of the cuff is adjusted so as to prevent the leakage of carbon dioxide past the cuff. The inflation of the cuff is adjusted to provide a minimum inflation pressure, which prevents leakage of carbon dioxide past the cuff.

Additional prior arts of relevance include U.S. Pat. Nos. 3,504,676, 3,794,036, 4,305,392, 4,770,170, 4,825,862, 5,067,497, 5,579,762, 5,582,166, 5,582,167, 5,752,921, 5,819,723, 5,937,861 and 6,062,223.

The present invention provides solutions to the problems associated with prior art endotracheal intubation techniques.

SUMMARY OF THE INVENTION

The background art does not teach the optimization of endotracheal tube cuff filling by measuring a measure indicative of secretion leakage past the cuff to the lungs and comparing the indicative measure with an optimal level of the measure. The background art does not teach the optimal value of carbon dioxide concentration nor does it teach any measure other than carbon dioxide concentration. Furthermore, the background art does not teach the use of additives to identify formation of leakage duct near the cuff for the purpose of cuff adjustment.

The present invention provides a method and system which can be efficiently used in intubation procedures in which an endotracheal tube is introduced into the tracheal airway and a cuff is inflated within the airway below the vocal cords.

In various exemplary embodiments of the invention the method and system of the present invention perform measurement of one or more measures being indicative of secretion leakage past the cuff, compare the measure(s) to one or more optimal values of the measure(s) and adjust cuff filling based on the comparison. The measure(s) according to preferred embodiments of the present invention can be carbon dioxide concentration, a proxy measure from which such concentration can be inferred, or the level of one or more additives delivered to a subject during intubation so as to identify formation of leakage duct near the cuff.

When one or more additives are delivered to the subject, they can be delivered either to the lungs, through the main lumen of the endotracheal tube (e.g., by mixing the breathing gas with the additive), or to a location above the cuff between the internal wall of the subject's airway and the external wall of the endotracheal tube. The level of the additive is monitored at a monitoring location which is selected according to the delivery technique. For example, when the delivery is through the main lumen of the endotracheal tube, the monitoring location can be above the cuff between the internal wall of the subject's airway and the external wall of the endotracheal tube; and when the delivery is to a location above the cuff between the airway and the endotracheal tube, the monitoring location can be below the cuff or within the main lumen of the endotracheal tube.

Thus, according to one aspect of the present invention there is provided a method of intubating a subject having a tracheal airway ending with lungs. The method comprises: inserting an endotracheal tube into the airway; inflating a cuff associated with the endotracheal tube within the airway below the vocal cords; measuring a level of at least one measure being indicative of leakage of secretion past the cuff to the lungs; comparing the level of the measure(s) with an optimal level of the measure(s); and adjusting inflation of the cuff based on the comparison so as to generally minimize leakage of secretion from above the cuff to the lungs, while minimizing pressure associated damages to the airway.

According to further features in preferred embodiments of the invention described below, the measure is other than carbon dioxide concentration between the cuff and the vocal cords According to still further features in the described preferred embodiments the method further comprises performing at least one measurement of ambient carbon dioxide partial pressure, and utilizing the ambient carbon dioxide partial pressure for setting the value of the optimal level.

According to still further features in the described preferred embodiments the measurement of ambient carbon dioxide partial pressure is performed continuously, so as to provide a series of real-time values of the ambient carbon dioxide partial pressure.

According to still further features in the described preferred embodiments the ambient carbon dioxide partial pressure is used as a reference partial pressure, whereby the optimal level corresponds to a carbon dioxide partial pressure being larger than the reference partial pressure by about 4 mm Hg.

According to still further features in the described preferred embodiments the optimal level corresponds to a partial carbon dioxide pressure of from about 0.32 mm Hg to about 4 mm Hg.

According to another aspect of the present invention there is provided a method of intubating a subject having an airway ending with lungs and vocal cords. The method comprises: inserting an endotracheal tube into the airway; inflating a cuff associated with the endotracheal tube within the airway below the vocal cords; delivering a breathing gas and at least one identifiable additive through the endotracheal tube; monitoring a level of the at least one identifiable additive at a monitoring location in the body of the subject; and adjusting inflation of the cuff based on the monitoring so as to generally minimize leakage of secretion from above the cuff to the lungs, while minimizing pressure associated damages to the airway.

According to further features in preferred embodiments of the invention described below, the method further comprises signaling when a level of the at least one identifiable additive exceeds an optimal level of the at least one identifiable additive.

According to still further features in the described preferred embodiments the monitoring location is at a nostril of the subject, oropharynx, above the cuff between the endotracheal tube and walls of the airway and/or below the cuff and adjacent thereto.

According to still further features in the described preferred embodiments the method further comprises suctioning secretions at a suctioning location in the airway above the cuff.

According to still further features in the described preferred embodiments the insertion of the endotracheal tube comprises inserting at least one of a measuring conduit and a suctioning conduit.

According to still further features in the described preferred embodiments adjustment of the cuff inflation is performed manually.

According to still further features in the described preferred embodiments adjustment of the cuff inflation is performed automatically.

According to yet another aspect of the present invention there is provided a system for intubating a subject having an airway ending with lungs, comprising: an endotracheal tube, adapted to be inserted into the airway and being associated with a cuff capable of being inflated below the vocal cords; and a measuring device for measuring at least one measure being indicative of leakage of secretion from above the cuff to the lungs.

According to further features in preferred embodiments of the invention described below, the measuring device is designed and configured to signal when a level of the at least one measure exceeds the optimal level.

According to still further features in the described preferred embodiments the system further comprises the optimal level is a predetermined optimal level.

According to still further features in the described preferred embodiments the measuring device is designed and configured to signal when a level of the measure(s) exceeds an optimal level corresponding to a partial carbon dioxide pressure of from about 0.32 mm Hg to about 4 mm Hg.

According to still further features in the described preferred embodiments the measuring device is designed an configured to perform at least one measurement of ambient carbon dioxide partial pressure, whereby the ambient carbon dioxide partial pressure is utilized for setting the value of the optimal level.

According to an additional aspect of the present invention there is provided a system for intubating a subject having an airway ending with lungs. The system comprises: an endotracheal tube, adapted to be inserted into the airway and being associated with a cuff capable of being inflated below the vocal cords; an additive delivering unit operatively associated with the endotracheal tube and configured to deliver at least one identifiable additive through the endotracheal tube; and a measuring device for measuring a level of the at least one identifiable additive.

According to further features in preferred embodiments of the invention described below, the measuring device is designed and configured to signal when a level of the at least one identifiable additive exceeds an optimal level of the at least one identifiable additive.

According to still further features in the described preferred embodiments the endotracheal tube comprises an additive delivery conduit configured to deliver the at least one identifiable additive.

According to still further features in the described preferred embodiments the additive delivery conduit is disposed within a lumen of the endotracheal tube.

According to still further features in the described preferred embodiments the additive delivery conduit is externally coupled to or embedded in a wall of the endotracheal tube.

According to still further features in the described preferred embodiments the system further comprises an inflating device for adjusting inflation of the cuff based on signals received from the measuring device so as to generally minimize leakage of secretion from above the cuff to the lungs, while minimizing pressure associated damages to the airway.

According to still further features in the described preferred embodiments the measuring device comprises a display device for displaying the level of the at least one measure.

According to still further features in the described preferred embodiments the system further comprises an alerting unit being in communication with the measuring device for producing an alert in response to signals received from the measuring device.

According to still further features in the described preferred embodiments the inflating device is in communication with the measuring device, thereby forming therewith a closed loop control.

According to still further features in the described preferred embodiments the system further comprises a measuring conduit extending from the measuring device to the airway above the cuff.

According to still further features in the described preferred embodiments the system further comprises a suctioning device operative for suctioning secretions at a suctioning location in the airway above the cuff.

According to still further features in the described preferred embodiments the system further comprises a suctioning conduit extending from the suctioning device to the suctioning location.

According to still further features in the described preferred embodiments the system further comprises a measuring and suctioning conduit, extending to the suctioning location, the a measuring and suctioning conduit being coupled to the measuring device and the suctioning device so as to facilitate the measuring and the suctioning at the location.

According to still further features in the described preferred embodiments the measuring and suctioning conduit is disposed internally within the endotracheal tube.

According to still further features in the described preferred embodiments the measuring and suctioning conduit is disposed externally to the endotracheal tube.

According to still further features in the described preferred embodiments the measuring and suctioning conduit is embedded in a wall of the endotracheal tube.

According to still further features in the described preferred embodiments the measurement is performed at a nostril of the subject.

According to still further features in the described preferred embodiments the measurement is performed at the oropharynx of the subject.

According to still further features in the described preferred embodiments the measurement is performed above the cuff below the vocal cords of the subject.

According to still further features in the described preferred embodiments the measurement is performed below the cuff and adjacent thereto.

According to still further features in the described preferred embodiments the at least one measure comprises carbon dioxide concentration between the cuff and the vocal cords.

According to still further features in the described preferred embodiments the at least one measure comprises carbon dioxide concentration above the vocal cords.

According to still further features in the described preferred embodiments the at least one measure comprises carbon dioxide concentration at a nostril of the subject.

According to still further features in the described preferred embodiments the at least one measure comprises acoustical data being indicative of leakage near the cuff outside the endotracheal tube.

According to still further features in the described preferred embodiments the measuring comprises filtering out background data from the acoustical data.

According to still further features in the described preferred embodiments the background data is characterized by a frequency being below about 1200 Hz.

According to still further features in the described preferred embodiments the measuring comprises calculating frequency difference characterizing the acoustical data, the frequency difference being induced by the Doppler effect.

According to still further features in the described preferred embodiments the measuring comprises calculating traveling time of acoustical signals and utilizing the traveling time for determining fluid flow near the cuff.

According to still further features in the described preferred embodiments the at least one measure comprises pressure data being indicative of fluid flow near the cuff outside the endotracheal tube.

According to still further features in the described preferred embodiments the at least one measure comprises flow data being indicative of fluid flow near the cuff outside the endotracheal tube.

According to still further features in the described preferred embodiments the at least one measure comprises optical data being indicative of presence of secretions near the cuff outside the endotracheal tube.

According to still further features in the described preferred embodiments the at least one measure comprises difference between inhaled and exhaled air volumes passing through the endotracheal tube.

According to still further features in the described preferred embodiments the at least one measure comprises electrical characteristics of fluid above the cuff outside the endotracheal tube.

According to still further features in the described preferred embodiments the monitoring of the level at least one identifiable additive is performed above the cuff below the vocal cords of the subject.

According to still further features in the described preferred embodiments the measuring device comprises a mass spectrometer. According to still further features in the described preferred embodiments the monitoring of the level of the at least one identifiable additive comprises performing mass spectrometry.

According to still further features in the described preferred embodiments the measuring device comprises a gas analyzer.

According to still further features in the described preferred embodiments the at least one identifiable additive is characterized by measurable electric properties. According to still further features in the described preferred embodiments the measuring device is capable of measuring the electric properties. According to still further features in the described preferred embodiments the monitoring of the at least one identifiable additive is by measuring the electric properties.

According to still further features in the described preferred embodiments the at least one identifiable additive is characterized by measurable magnetic properties. According to still further features in the described preferred embodiments the measuring device is capable of measuring the magnetic properties. According to still further features in the described preferred embodiments the monitoring the at least one identifiable additive is by measuring the magnetic properties.

According to still further features in the described preferred embodiments the at least one identifiable is characterized by measurable optical properties. According to still further features in the described preferred embodiments the measuring device is capable of measuring the optical properties. According to still further features in the described preferred embodiments the monitoring the at least one identifiable additive is by measuring the optical properties.

According to still further features in the described preferred embodiments the at least one identifiable is characterized by measurable radiative properties. According to still further features in the described preferred embodiments the measuring device is capable of measuring the radiation properties. According to still further features in the described preferred embodiments the monitoring the at least one identifiable additive is by measuring the radiation properties.

According to still further features in the described preferred embodiments the at least one identifiable is characterized by measurable fluorescent properties. According to still further features in the described preferred embodiments the measuring device is capable of measuring the fluorescent properties. According to still further features in the described preferred embodiments the monitoring the at least one identifiable additive is by measuring the fluorescent properties.

According to still further features in the described preferred embodiments the at least one identifiable additive comprises at least one inert gas. According to still further features in the described preferred embodiments the at least one inert gas is selected from the group consisting of comprises helium and krypton.

According to still further features in the described preferred embodiments the at least one identifiable additive comprises at least one colored gas.

According to still further features in the described preferred embodiments the at least one identifiable additive comprises at least one radioisotope. According to still further features in the described preferred embodiments the at least one radioisotope is selected from the group consisting of a technetium radioisotope, a xenon radioisotope and a krypton radioisotope.

The present invention successfully addresses the shortcomings of the presently known configurations by providing a system and method for performing endotracheal intubation and optimizing endotracheal tube cuff filling.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present embodiments comprise a method and system which can be used for intubation. Specifically, the present invention can be used for optimizing endotracheal tube cuff filling.

Figure 1:
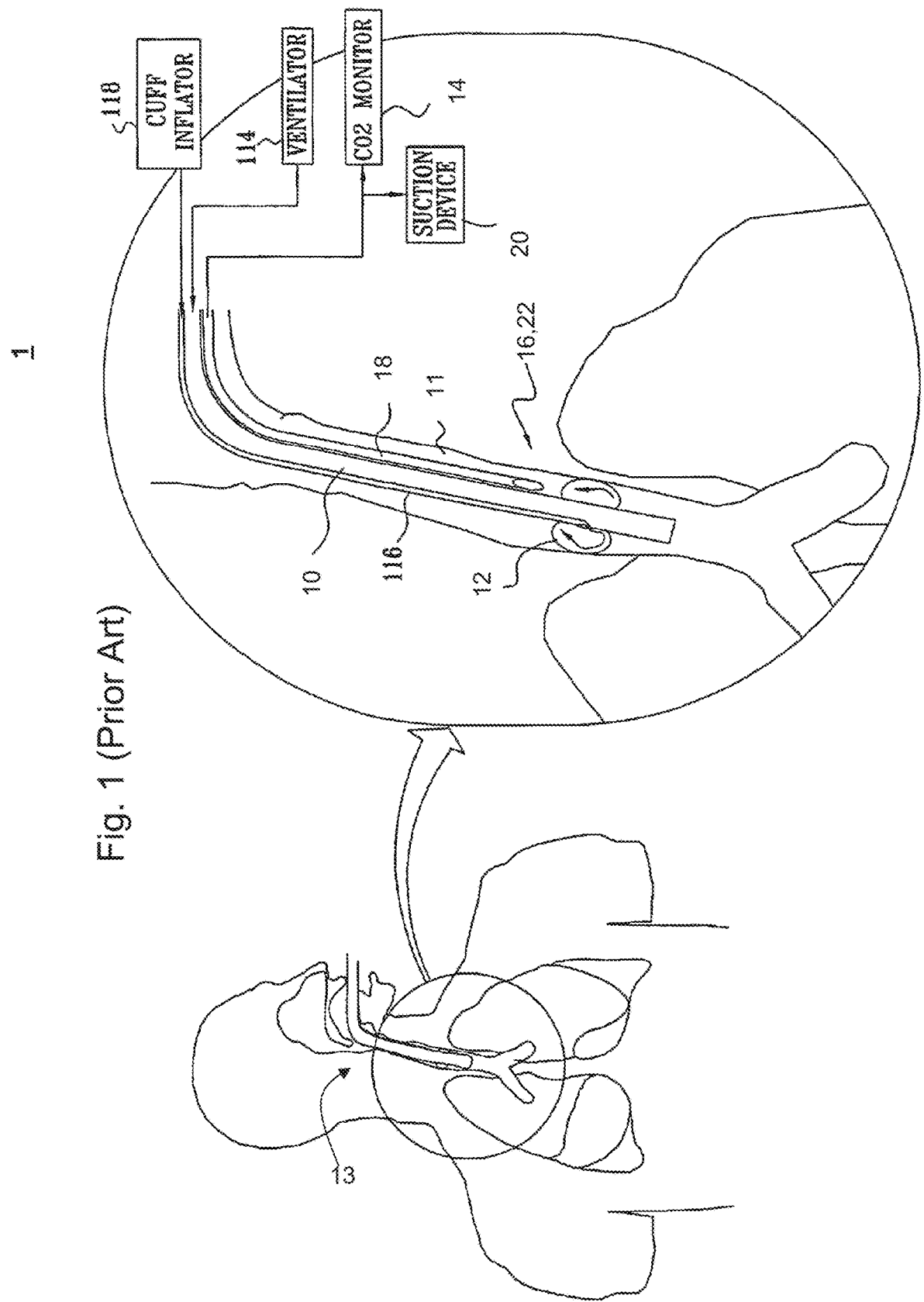
FIG. 1 is a schematic illustration of a prior art intubation system.

For purposes of better understanding the present invention, as illustrated in FIGS. 2-15 of the drawings, reference is first made to the construction and operation of a conventional (i.e., prior art) intubation system as illustrated in FIG. 1.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a prior art intubation system invented by the same inventor as the present invention, generally referred to herein as system 1. System 1 comprises an endotracheal tube 10 which is inserted into a patient airway. An inflatable cuff 12 is associated with tube 10 and arranged to be located at a location in the patient airway 11 below the vocal cords 13. Tube 10 is coupled to a ventilator 114 and the inflatable cuff 12 is connected to a cuff inflator 118, via inflation conduit 116.

System 1 further comprises a carbon dioxide ($CO_2$) monitor 14 which monitors $CO_2$ concentration in airway 11 at a $CO_2$ monitoring location 16 above cuff 12. Monitor 14 is coupled to location 16 via a $CO_2$ monitoring conduit 18. Additionally, system 1 comprises a suctioning device 20 for suctioning secretions at a suctioning location 22 above cuff 12.

Monitor 14 provides an indication of the sealing of airway 11 by cuff 12 thereby increases the respiration efficiency and reduces pressure related damage to airway 11. The operation of suctioning device 20 further improves the intubation process by removing secretions upstream of cuff 12 so as prevent the secretions from entering airway 11 downstream of cuff 12. This prevention is the result of the combination of effective sealing of airway 11 and removal of secretions upstream of cuff 12.

The $CO_2$ serves as an indicator for the leakage of secretions into the lungs. System 1 is therefore directed to the detection of $CO_2$ above the cuff. Any presence of $CO_2$ above the cuff is used by system 1 as an indicator for secretions leakage into the lungs.

The performances of system 1 above, however, are not optimal. This is because there is no indication whether the airway is sealed under the optimal conditions. Although the presence of $CO_2$ above the cuff may indicate the leakage of secretions into the lunge, it is not always the case. Due to the viscosity of the secretions in the airway, there are situations in which the cuff is not completely sealed for passage of air, and yet there is no leakage of secretions into the lungs. Under such conditions, it is desired not to increase the cuff pressure, so as not to cause pressure related damage to the tissues contacting the cuff.

Figure 2:
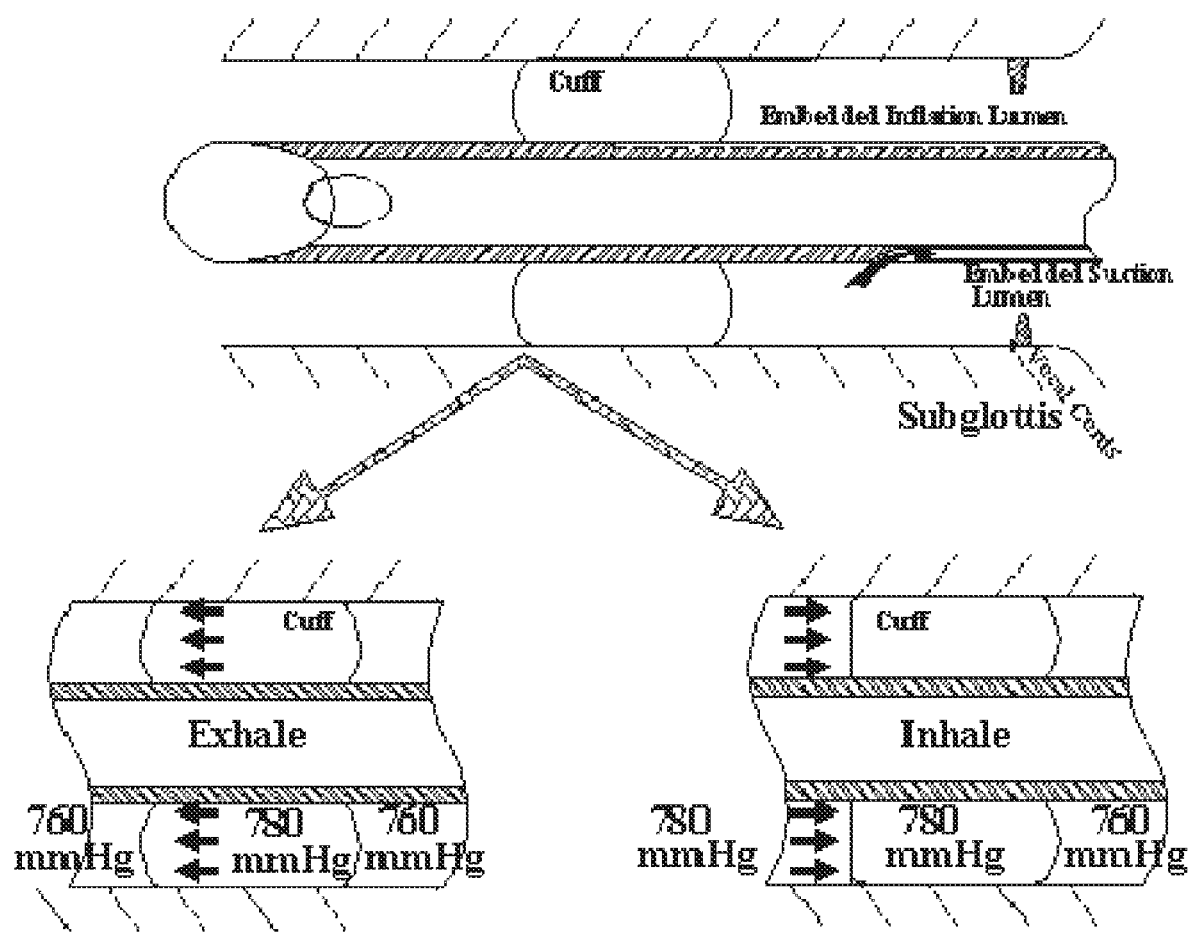
FIG. 2 is a schematic illustration of an endotracheal tube cuff during inhalation and exhalation.

FIG. 2 illustrate the problems associated with leakage of secretions past the cuff. Typically, the contact area between the cuff and the trachea is about 2600-3200 mm$^2$ on a generally cylindrical inner wall, about 75-80 mm in perimeter and about 35-40 mm in length. The secretions leakage begins when open ducts are formed between the cuff and the inner wall of the trachea. The open ducts are formed due to changes in temperature, posture of the subject and the like. These changes are supplemented by the periodic operation of the breathing or anesthesia machine. The pressure below the cuff increases to about 780 mm Hg during inhalation, and decreases to about 760 mm Hg (at sea level) during exhalation. This periodic process generates relative motion between the cuff and the inner wall of the trachea, resulting in the formation of the aforementioned open ducts.

Under such conditions, secretions produced at the subglottis begin to penetrate into small volumes formed between the surfaces of the cuff and the tracheal wall. The secretions are subjected to several forces: gravity (patient is tilted about 30-45 degrees above to horizontal orientation), external friction (applied by the surfaces of tracheal wall and the cuff), internal friction (viscosity of the secretions), pressure difference of about 20 mm Hg during inhalation, capillarity and gravity. The direction of the resulting effective force is typically to the lungs, resulting in leakage of secretions and potential damage to the subject.

The situation is aggravated over time because the interaction between the secretions and air passing outside the endotracheal tube, results in solidification of the secretions. Under such circumstances, any small change in the posture of the subject increases the leakage of newly formed secretions into the lungs.

It is therefore the object of the present invention to provide a method and system which allow the identification of leakage formation at an early stage so as to timely and optimally adjust the inflation pressure of the cuff. While conceiving the present invention it has been hypothesized and while reducing the present invention to practice it has been realized that damage to the intubated subject can be significantly reduced if the intubation system operates under optimal conditions which are defined prior to the intubation procedure.

Figure 3A:
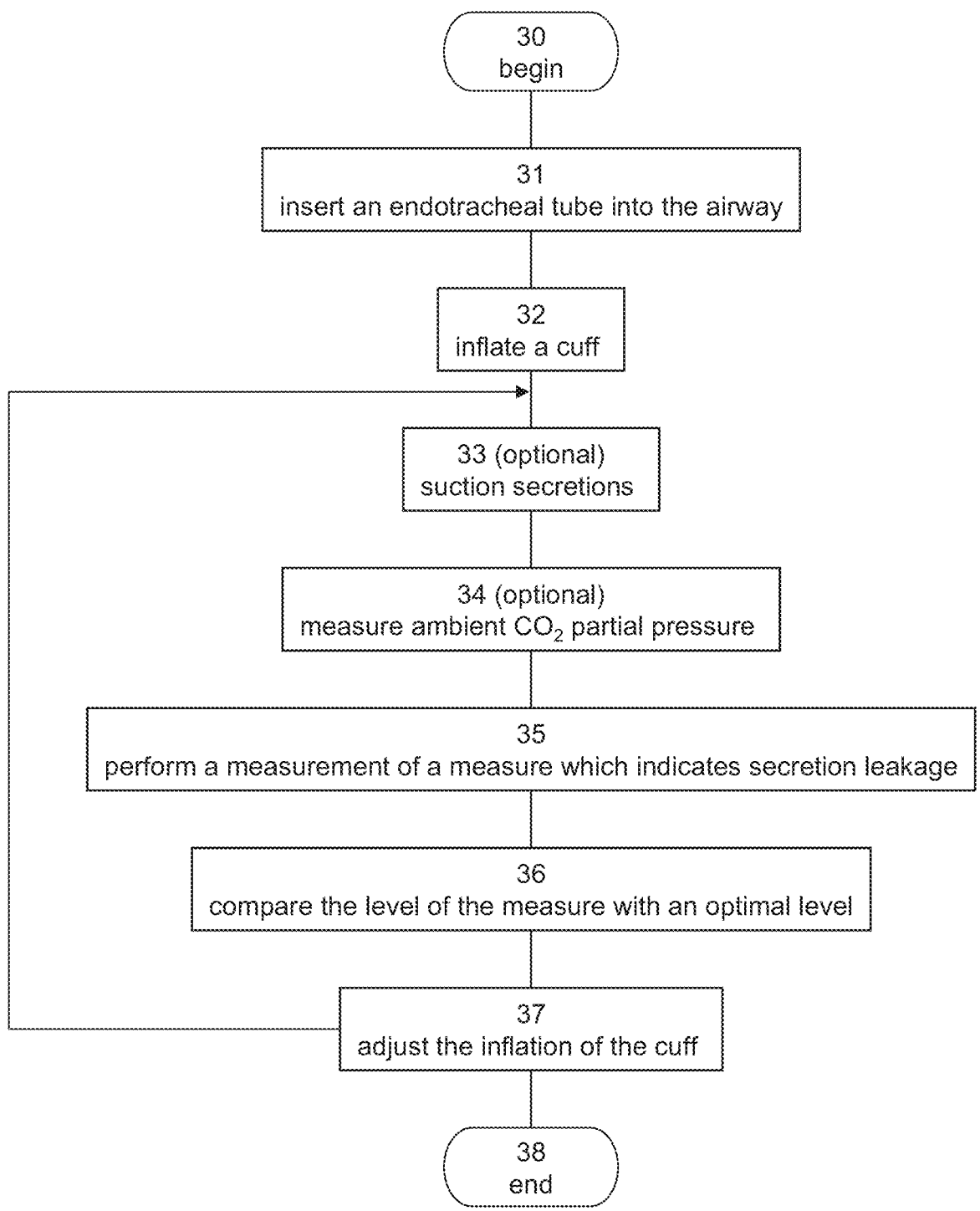
FIGS. 3a-c are flowchart diagrams of a method suitable for intubating a subject, according to various exemplary embodiments of the present invention.
Figure 3B:
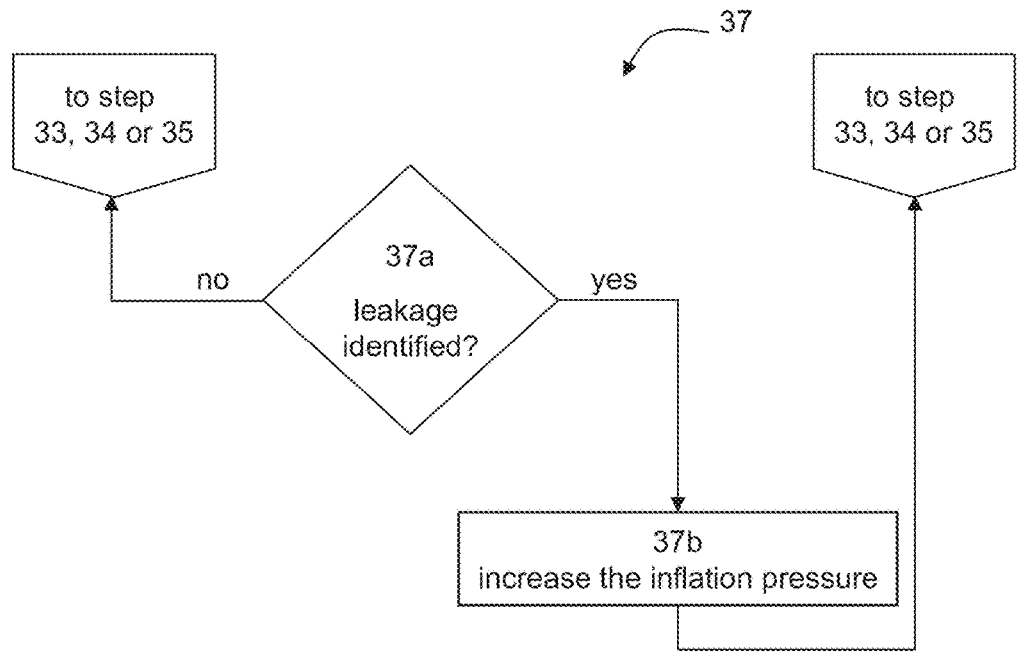
Figure 3C:
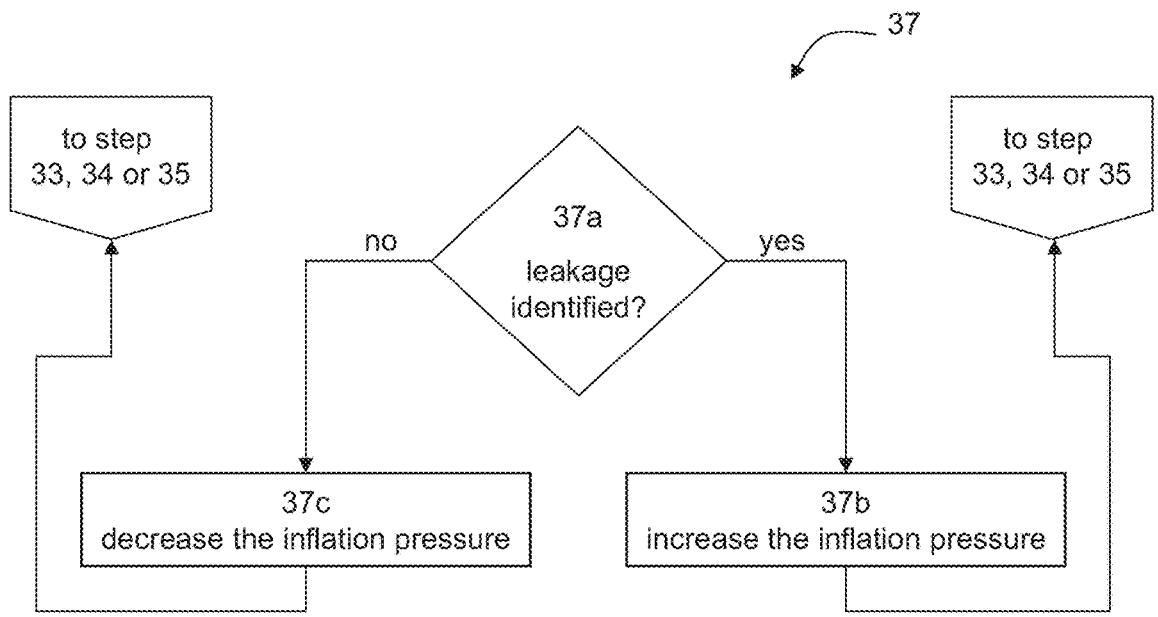

Reference is now made to FIGS. 3a-c which are flowchart diagrams of a method suitable intubating a subject, according to various exemplary embodiments of the present invention.

It is to be understood that, unless otherwise defined, the method steps described hereinbelow can be executed either contemporaneously or sequentially in many combinations or orders of execution. Specifically, the ordering of the flowchart diagrams provided herewith is not to be considered as limiting. For example, two or more method steps, appearing in the following description or in a particular flowchart diagram in a particular order, can be executed in a different order (e.g., a reverse order) or substantially contemporaneously. Additionally, several method steps described below are optional and may not be executed.

The method begins at step 30 and continues to step 31 in which an endotracheal tube is inserted into the airway of the subject. The method continues to step 32 in which a cuff associated with the endotracheal tube is inflated within the airway below the vocal cords of the subject. In various exemplary embodiments of the invention the method continues to optional step 33 in which secretions are suctioned at a suctioning location in the airway above the cuff. In the embodiments in which the optional suctioning step is executed, it can be performed either in an alternating, continuous or contemporaneous manner with any of the other method steps described below. For example, step 33 can be performed in a continuous manner contemporaneously with a sequential execution of steps 34-37 or 35-37 described below. Alternatively, step 33 can be executed whenever the method loops back from step 37.

There are several advantages for executing the suctioning step not contemporaneously with other steps of the method.

One advantage is that continuous suctioning of secretions can damage the mucosal membrane of the subglottis. Intermittent execution of the suctioning step relieves the continuous load on the tissue.

Another advantage is that time separation between the suctioning step and the other steps reduces or eliminates the influence of the suctioning operation on the results of leakage identification. As further explained below, the leakage identification is preferably based on measurement of one or more measures which are indicative of secretions leakage past the cuff into the lungs. When the suctioning operation is performed contemporaneously with the measuring step, it can influence on the measurement by altering the level of the leakage-indicating measure. For example, as will be explained below, in one embodiment, the leakage-indicating measure is a $CO_2$ concentration or partial pressure. The execution of the suctioning step not contemporaneously with the measurement of $CO_2$ concentration or partial level, eliminates the interference between the suctioning and the measurement, because the concentration or partial pressure of $CO_2$ is not changed by the suctioning device during the measurement. Since the suction power of the suctioning device is typically higher than the pumping power of $CO_2$, time separation between the suctioning step and the $CO_2$ measuring step prevent obstruction of the $CO_2$ measurement by the suctioning device.

Furthermore, the execution of the suctioning step prior to the measurement allows the measurement to be performed in a substantially secretions-free environment, thus improving the efficiency and accuracy of the measurement.

According to a preferred embodiment of the present invention the insertion of the endotracheal tube is accompanied by the insertion of suctioning conduit to facilitate the execution of the optional suctioning step.

In various exemplary embodiments of the invention the method comprises an optional step 34 in which ambient $CO_2$ partial pressure is measured. The measurement is preferably performed in the immediate surroundings of the subject. For example, when the intubation is performed in the emergency room, the ambulatory transportation vehicle, the operating room and the like. In the embodiment in which step 34 is performed, the ambient $CO_2$ partial pressure is utilized for setting a reference value for the measurement or measurements performed in step 35 described below. The ambient $CO_2$ partial pressure measurement can be performed once, before or after the insertion of the endotracheal tube into the airway, or, more preferably, in a continuous manner throughout the procedure, e.g., contemporaneously with step 33. In this embodiment, a series of real-time values for the ambient $CO_2$ partial pressure is preferably provided. Alternatively, the ambient $CO_2$ partial pressure measurement can be performed in an alternating manner with any of the method steps. For example, the measurement can be performed alternatively with step 35. The reference ambient value can be measured while the system is in suction process. Since the rate of change in the ambient $CO_2$ partial pressure is expected to be low, the ambient measurement can be performed, e.g., once per hour or even once per 2 hours.

Whether or not the optional steps are executed, the method continues to step 35 in which a measurement of a measure being indicative of leakage is performed. Many measures are contemplated. Generally, the measure can be any quantity whose level is in correlation with leakage of secretions past cuff to the lungs. Measurements of several different measures can also be performed so as to increase the accuracy of the procedure. In this case, all the measures are preferably weighted using a predetermined set of weights which may correspond, for example, to the relative accuracy level of each measure and/or its correlation level with the secretions leakage. Typically, but not obligatorily, the measure can be concentration of $CO_2$ above cuff or a proxy measure from which such concentration can be inferred. Representative examples of leakage-indicating measures are provided hereinafter. The measurement is performed using one or more measuring devices suitable for measuring the selected leakage-indicating measure(s). According to a preferred embodiment of the present invention the insertion of the endotracheal tube is accompanied by the insertion of a communication device (e.g., a conduit) which communicates with the measuring device(s).

The measurement of step 35 is performed at a measurement location which is accessible to the measuring device or the communication device. Preferably, the measurement location is selected so as to optimize the accuracy of the measurement while minimizing discomfort to the subject. Thus, for example, the measurement location can be at the nostril of the subject, between the cuff and the vocal cords, above the vocal cords (e.g., at the oropharynx) and/or below cuff and adjacent thereto. Whereas the nostril or oropharynx are more convenient measurement locations to the operator and patient, performing the measuring near the cuff is more preferred from the standpoint of the measurement accuracy and analysis reliability.

Once the leakage-indicating measure is obtained the method continues to step 36 in which the level of the measure is compared with an optimal reference level of the measure. According to a preferred embodiment of the present invention the optimal level is predetermined. The optimal level can also be updated periodically by measuring ambient level, as in the case of, e.g., $CO_2$. In the preferred embodiment in which measurements of more than one measure are performed, the level of each measure is preferably compared with a respective optimal reference level.

The optimal level is preferably the maximal level of the respective measure which is indicative to a negligibly low or no leakage of secretions from above the cuff into the lung. Thus, the optimal level enacts a leakage identification threshold. As long as the level of the measure is below the threshold, the leakage is considered negligible (or nonexistent) and the airway is considered properly sealed. The threshold is typically a lower bound, so that secretions leakage is identified at the location of the cuff whenever the level of the measure exceeds the threshold. Alternatively, the threshold can be defined as an upper bound in which case so that secretions leakage is identified at the location of the cuff whenever the level of the measure is below the threshold.

The optimal reference level can be extracted from studies directed to determine this level, tables, charts, graphs or formulae obtained by empirical considerations and/or theoretical calculations. For example, in experiments performed by the inventor of the present invention it was found that there is a leakage of secretions when the partial pressure of $CO_2$ is well above the typical atmospheric $CO_2$ partial pressure (about 0.03%, or about 0.26-0.32 mm Hg).

Thus, in the embodiment in which the leakage-indicating measure is partial pressure of $CO_2$, the optimal level of is preferably P mm Hg, where P is a partial pressure which is above the ambient $CO_2$ partial pressure, $P_{ref}$. $P_{ref}$ can be known in advance (before the intubation procedure), or, more preferably, can be measured during the execution procedure, as further detailed hereinabove. Denoting by $\Delta P$ the (positive) difference $P-P_{ref}$, $\Delta P$ is preferably lower or equal about 4 mm Hg, more preferably lower or equal about 2 mm Hg, more preferably lower or equal about 1 mm Hg, even more preferably lower or equal about 0.4 mm Hg. For example, assuming a hospital ventilation rate standards as 40 cubic feet per minute per person (to this end see, e.g., Air-Conditioning Engineers (ASHRAE) Standard 62-1989 Ventilation Standard for Acceptable Air), P can be from about 0.32 mm Hg to about 4 mm Hg, more preferably from about 0.32 mm Hg to about 2 mm Hg, more preferably from about 0.32 mm Hg to about 1 mm Hg, even more preferably from about 0.32 mm Hg to about 0.7 mm Hg.

As used herein the term "about" refers to ±10%.

The leakage-indicating measure can also be a measure other than $CO_2$ concentration. In this embodiment, the leakage-indicating measure is preferably a proxy measure from which the presence or level of leakage can be inferred. For example, the leakage-indicating measure can be a proxy measure to $CO_2$ concentration or $CO_2$ partial pressure. In this embodiment, the optimal level can be the level of the proxy measure which corresponds to the optimal level of $CO_2$ concentration or $CO_2$ partial pressure, as further detailed hereinabove.

From the comparison step 36, the method proceeds to step 37 in which the inflation of the cuff is adjusted, based on the comparison to the optimal level. The adjustment is performed in a manner such that both leakage of secretion and occurrences of pressure associated damages are generally minimized. This is preferably done by reducing the cuff pressure and then raising it gradually to the desired optimal level. Before pressure reduction the suctioning step is preferably executed to clear the space of secretions. From step 37 the method, optionally and preferably, loops back to step 33 or step 35.

Two alternative and optional execution procedures for step 37 are illustrated in the partial flowcharts of FIGS. 3b-c. Hence, from step 36 (not shown, see FIG. 3a) the method continues to decision step 37a in which the method decides whether or not the level of the leakage-indicating measure exceeds the optimal level. If the optimal level is exceeded, a non-negligible leakage has been identified and the method continues to process step 37b in which the inflation pressure of the cuff is increased so as to provide better sealing. If optimal level is not exceeded, the method can either loop back to step 33 or step 35 without changing the inflation pressure (FIG. 3b), or proceed to step 37c in which the inflation pressure of the cuff is decreased (FIG. 3c). From step 37c the method preferably loops back to step 33 or step 35. The advantage of the embodiment of FIG. 3c is that it allows further optimization of the inflation pressure in the cuff. The inflation pressure in the cuff can be decreased as long as the leakage is sufficiently low or there is no leakage.

Thus, the method of the present embodiment provides a closed loop control on the inflation of the cuff, such that leakage of secretions is minimized or substantially prevented with a minimal local pressure on the trachea. Such control facilitates an efficient breathing assistance to the subject with minimal risk to lung infections or pressure related damage to the airway's wall.

The method ends at step 38.

As stated, the leakage-indicating measure can be any quantity whose level is in correlation with leakage of secretions past cuff to the lungs. Following are representative examples of leakage-indicating measures which can be measured, in various exemplary embodiments of the invention.

Hence, in one embodiment, the measure comprises $CO_2$ concentration or partial pressure. The measurement can be performed using a $CO_2$ concentration or partial pressure measuring device (e.g., a $CO_2$ analyzer), which can be located in or communicate with a measuring location, either between the cuff and the vocal cords, preferably close to the cuff, or at another location, such as, but not limited to, above the vocal cords (e.g., the oropharynx) or at the nostril. For $CO_2$ concentration, the optimal predetermined level (leakage identification threshold) can be, as stated, a $CO_2$ partial pressure which is above the ambient $CO_2$ partial pressure (e.g., from about 0.32 mm Hg to about 4 mm Hg). More specific values for the optimal predetermined level can be defined based on the location at which the $CO_2$ concentration or partial pressure is measured.

Figure 4A:
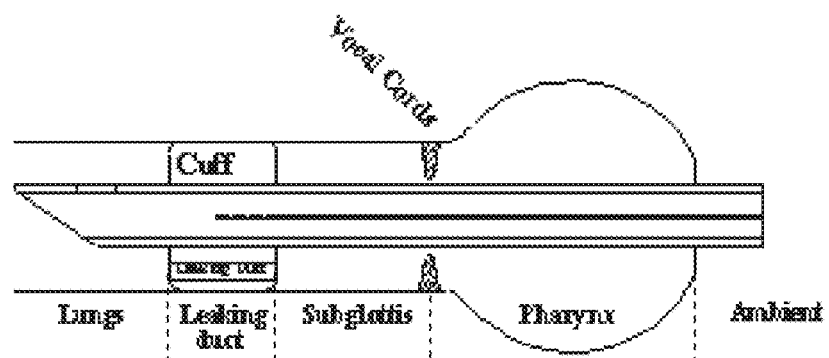
FIGS. 4a-b show partial $CO_2$ pressure at different measuring locations, in various exemplary embodiments of the invention.
Figure 4B:
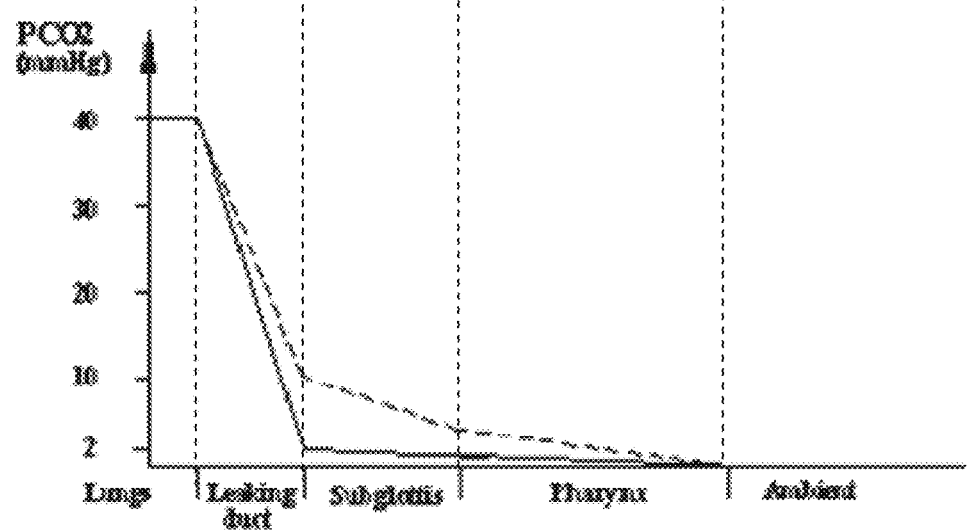

Reference is now made to FIGS. 4a-b, which show the partial $CO_2$ pressure, denoted $PCO_2$, at different measuring locations. The solid and dash lines in FIG. 4b represent partial $CO_2$ pressure gradients, for different leaking duct diameters. The partial $CO_2$ pressure exhaled of the lungs is typically 30-40 mm Hg (in a healthy person), while the ambient partial $CO_2$ pressure is about 0.26-0.32 mm Hg. As shown in FIG. 4b, there are different pressure drops between different locations along the path starting from the cuff and ending at the ambient environment (as function of the leaking the volumetric leaking rate). Along the leaking duct, formed between the cuff and the tracheal wall, the partial $CO_2$, the pressure drops from about 40 mm Hg at the lung to about 2 mm Hg at the opposite side of the cuff (solid line); along the subglottis, the pressure drops from about 2 mm Hg near the cuff to about 1 mm Hg at the vocal cords; within the pharynx, the pressure drops further to the ambient pressure.

Thus, when the measuring location is near the cuff (between the cuff and the vocal cords) the optimal predetermined level can be from about 0.32 mm Hg to about 4 mm Hg, and when the measuring location above the vocal cords or at the nostril the optimal predetermined level can be from about 0.32 to about 1 mm Hg. Other values are also contemplated.

The measurement of partial $CO_2$ pressure is preferably performed using a measuring device having a wide dynamic range. More preferably the measuring device of the present embodiments combines a high-sensitivity $CO_2$ sensor having a narrow dynamic range with a low-sensitivity $CO_2$ sensor having a wide dynamic range. For example, the high-sensitivity $CO_2$ sensor can have a sensitivity of about 0.02 mmHg and a dynamic range of about 0-1 mm Hg, and the low-sensitivity $CO_2$ sensor can have a sensitivity of about 0.1 mmHg and a dynamic range of about 1-10 mm Hg. When the measurement is performed above the vocal cords or at the nostril, the dynamic range of the measuring device can be lower (e.g., 0-1 mm Hg) with and the accuracy can be higher (e.g., 0.01 mm Hg).

In another embodiment, the measure comprises acoustical data being indicative of leakage near the cuff outside the endotracheal tube. The acoustical data can be collected using an acoustical measuring device, which can be positioned, for example, above and/or below the cuff adjacent to the leaking duct. Acoustical measuring devices suitable to be introduced into the trachea are known in the art and found, e.g., in U.S. Pat. Nos. 5,655,518, 5,890,488, 6,168,568, 6,261,238 and 6,383,142, the contents of which are hereby incorporated by reference.

The ability to identify the formation of a leaking duct using acoustical device is attributed to the unidirectional flow of air through the duct. The airflow through the leaking duct is unidirectional from the following reason. During the breathing cycle, the air pressure within the lungs is changed periodically. In the inhalation stage, the breathing machine increases the air pressure in the lungs and a pressure drop of about 20 mm Hg is built between the lungs and the subglottis. This pressure drop results in airflow from the lungs to the subglottis through the leaking duct. On the exit from duct the air expands with the volume of the subglottis. This expansion continues throughout the inhaling stage.

The magnitude of the air flow through the duct varies from zero (when the air pressure in the lungs equals the ambient air pressure) to a maximal value (when the air pressure in the lungs is maximal, e.g., about 20 mm Hg above ambient air pressure). The maximal magnitude of flow depends on the cross-sectional area of the duct.

Figure 5A:
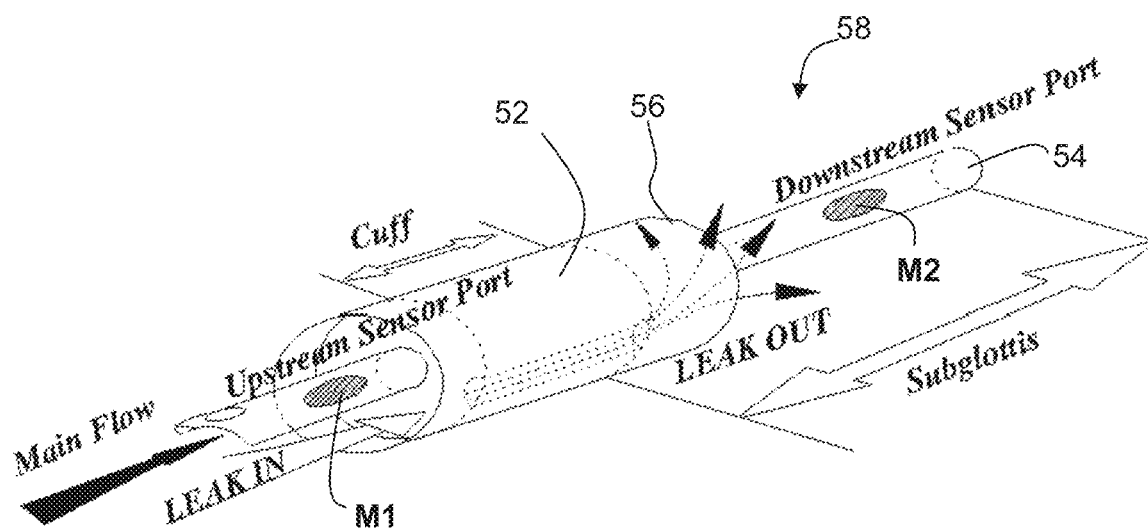
FIGS. 5a-b are schematic illustrations of the location of an acoustical measuring device, according to various exemplary embodiments of the present invention.
Figure 5B:
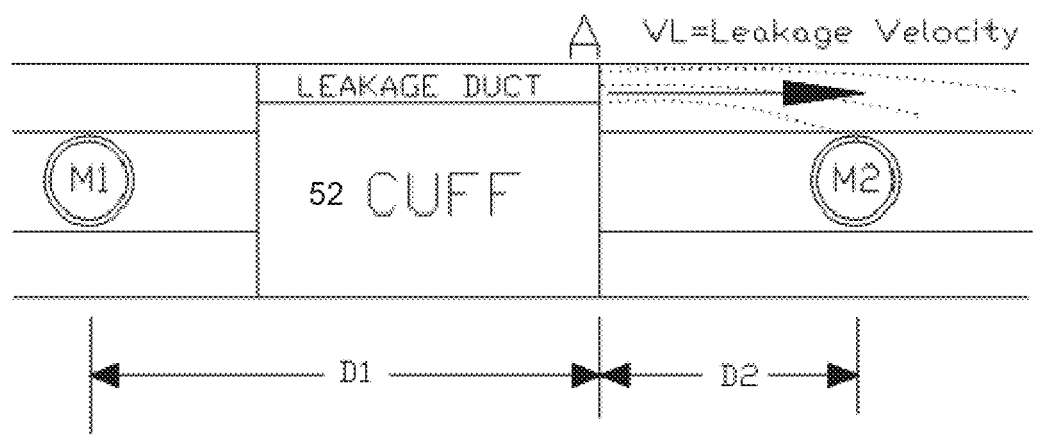

FIGS. 5a-b are schematic illustrations of the location of an acoustical measuring device 58, according to a preferred embodiment of the present invention. Shown in FIG. 5a is a trachea 56, an endotracheal tube 54 positioned within trachea 56 and a cuff 52 inflated between the external wall of tube 54 and the internal wall of trachea 56. Acoustical measuring device 58 preferably comprises a downstream sensor M2 and an upstream sensor M1. Sensors M1 and M2 serve for sensing sound waves impinging thereon. Being spaced apart from each other, the acoustical data collected by each sensor port is different, inter alia, due to different relative flow direction (outgoing with respect to sensor M1 and incoming with respect to sensor M2), as further explained hereinunder. The difference in acoustical data can be used to improve the sensitivity of device 58, as further detailed hereinbelow with reference to FIG. 5b.

Figure 5C:
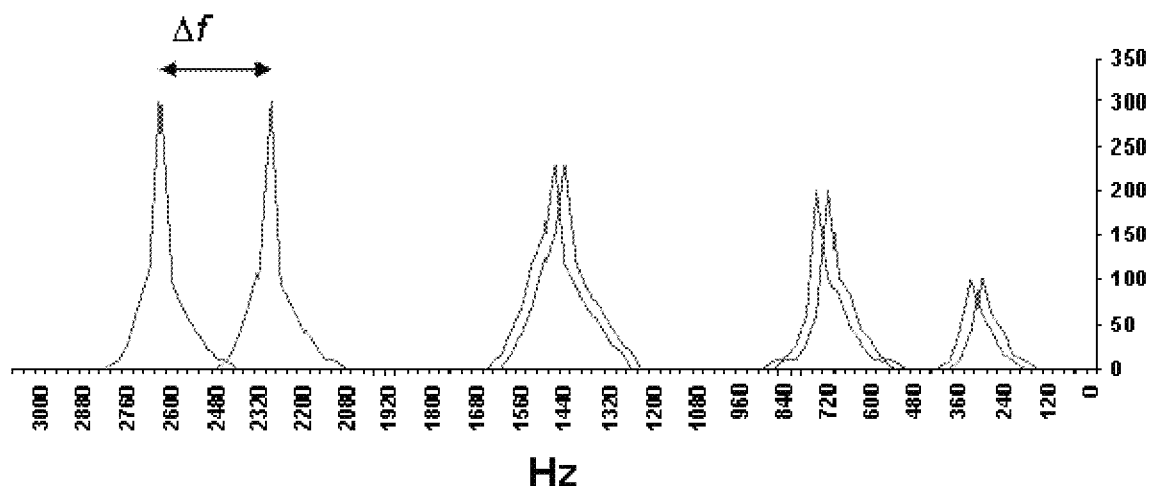
FIG. 5c shows a representative example of a procedure for identifying leakage by the Doppler effect, according to various exemplary embodiments of the present invention.

When leakage exists between sensors M1 and M2, due to the different relative flow direction and in accordance with the well-known Doppler effect, the acoustical signal sensed by sensor M2 has a higher frequency compared to the acoustical signal sensed by sensor M1. Thus, defining the frequency difference between the acoustical signals sensed by M1 and M2 by $\Delta f = f_2 - f_1$, where $f_1$ is the frequency sensed by M1 and $f_2$ is the frequency sensed by M2, a leakage can be identified when $\Delta f$ is higher than about 20 Hz. A representative example of leakage identification by Doppler effect is shown in FIG. 5c.

An additional method for identifying leakage is based on the traveling time of the acoustic sound from sensor M1 to sensor M2.

Air coming out of the lungs through the leaking duct accelerates by the influence of the pressure in the lungs. The acoustic signal arrives to sensor M1 at a velocity, $v_1$, which is the difference between the velocity of sound, $v_a$ (about 340 m/s), and the velocity of the air flowing in the leaking duct, $v_L$:

$$v_1 = v_a - v_L. \quad \text{(EQ. 1)}$$

The acoustic signal arrives to sensor M2 at a velocity, $v_2$, which is the sum of $v_a$ and $v_L$:

$$v_2 = v_a + v_L. \quad \text{(EQ. 2)}$$

The distances between the source of the acoustical signal and sensors M1 and M2 are denoted $d_1$ and $d_2$, respectively. The traveling times of the acoustic signal to M1 and M2 are, therefore, $t_1 = d_1/v_1$ and $t_2 = d_2/v_2$, respectively. In the following, for the purpose of simplicity, $d_1$ and $d_2$ are assumed to be equal, $$d_1 = d_2 \equiv d. \quad \text{(EQ. 3)}$$

The difference in the traveling times is a measurable quantity. Denoting this difference by $\Delta t$ one obtains from Equations 1-3:

$$\Delta t = d/(v_a - v_L) - d/(v_a + v_L), \quad \text{(EQ. 4)}$$

or $$\Delta t = 2d\, v_L/(v_a - v_L)(v_a + v_L) \approx 2d\, v_L/v_a^2 \quad \text{(EQ. 5)}$$

where in the last step, the square of the $v_L$ was neglected compared to the square of the $v_a$.

As can be understood from Equation 5 above, knowing the value of $\Delta t$, d and $v_a$, the value of $v_L$, hence also the presence of leakage, can be identified. Thus, according to the presently preferred embodiment of the invention the leakage-indicating measure is in correlation with the velocity, $v_L$. In this embodiment, the optimal level preferably corresponds to a velocity of from about 1 m/s to about 3 m/s.

Figure 5D:
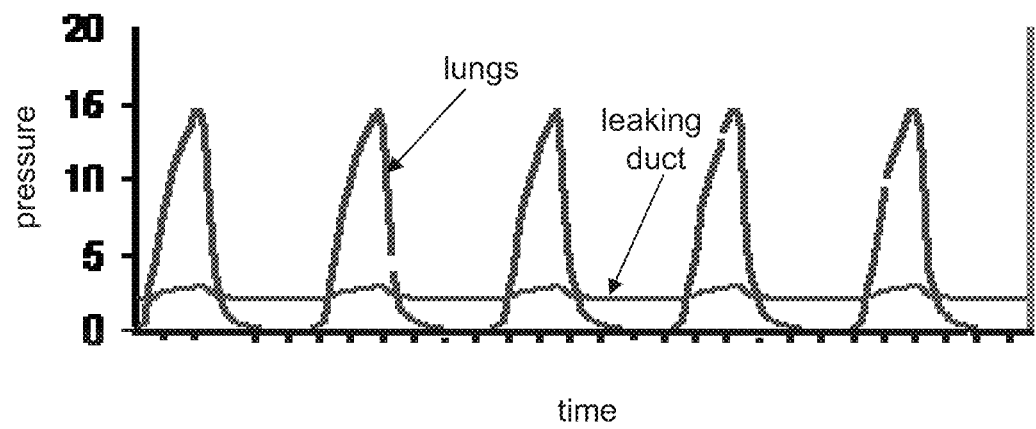
FIG. 5d shows the difference between the functional dependences of the pressure in the lungs and the pressure in a leaking duct during a breathing cycle, according to various exemplary embodiments of the present invention.

The measurement of acoustical data is preferably performed such that background noise is filtered out. The background noise can include all acoustical data associated with phenomena other than leakage of fluid through the leaking duct. Most of the background noise is generated by the breathing machine. During the exhalation stage of the machine (inhalation stage of the subject), the flow in a direction which is opposite to the unidirectional flow through the leaking duct. This is because the air expands, between the cuff and the lungs, from the low diameter of endotracheal tube to the larger diameter of the trachea. During the inhalation stage of the machine (exhalation stage of the subject), the air is compressed again. Thus, the background noise is characterized by oscillatory behavior (from compression to expansion and vise verse) whereas the flow through the leaking duct is unidirectional. The difference between the functional dependences of the pressure in the lungs and the pressure in the leaking duct during the breathing cycle is shown in FIG. 5d.

The filtering of the background noise can be done by spectral analysis of the collected acoustical data. Generally, acoustical data characterized by frequencies of from about 1200 Hz to about 2500 Hz, can be identified as proxy to the leakage. Other acoustical data can be associated with breathing, berating disorders, hoarseness and motion of muscles, such as the heart and lungs. Although acoustical data associated with breathing typically includes low frequencies (below 300 Hz), intermediate frequencies (between 300 and 600 Hz) and high frequencies (between 600 and 1200 Hz), most of the breathing energy is at the range of 60-600 Hz. Acoustical data associated with motion of the heart and lungs is typically in the low frequencies. Acoustical data associated with berating disorders or hoarseness are typically above the 2000 Hz.

The identification of acoustical data to be excluded can also be performed by performing a calibration step in which the acoustical measurements are performed sufficiently far from the leaking duct so as to define the background noise. Once the background noise is defined it can be subtracted from data collected near the cuff.

In an additional embodiment, the leakage-indicating measure comprises pressure data being indicative of fluid flow near the cuff outside endotracheal tube. Pressure data can be measured using a pressure measuring device.

Figure 6A:
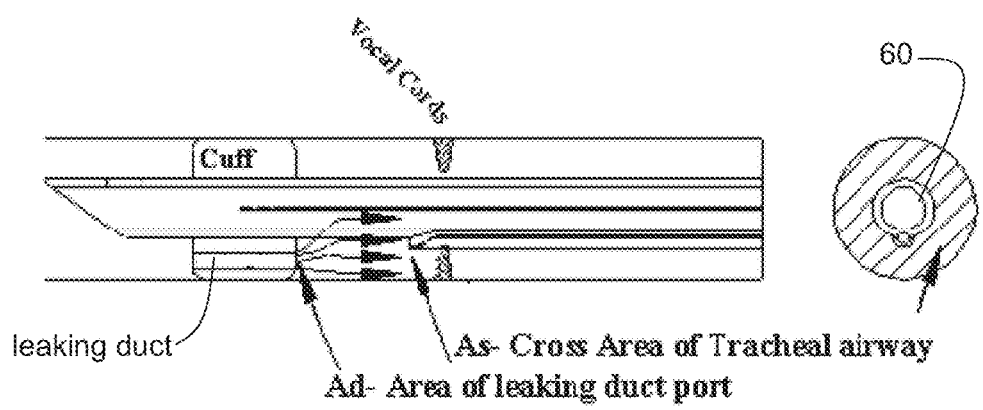
FIGS. 6a-b are schematic illustrations of the flow of air (FIG. 6a) and the pressure (FIG. 6b), in the trachea outside the endotracheal tube.
Figure 6B:
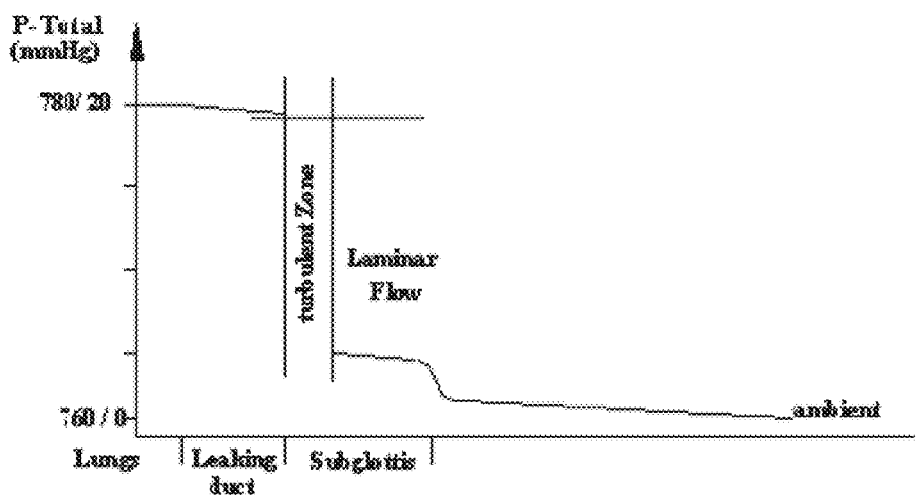

FIGS. 6a-b are schematic illustrations of the flow of air (FIG. 6a) and the pressure (FIG. 6b), in the trachea outside the endotracheal tube. The stagnation pressure in the lung during the inhalation stage is about 780 mm Hg, which, as stated, is about 20 mm Hg above the ambient pressure. The air flowing through the leaking duct enters the subglottis in turbulent flow. By the time the air reach the end of the subglottis (near the vocal cords) the flow becomes laminar.

Thus, according to a preferred embodiment of the present invention the pressure is measured at the pressure measuring location within the subglottis. The location is preferably near the vocal cords, where the airflow is substantially laminar. The air pressure, $P_{sd}$, at the pressure measuring location decreases according to the equation:

$$P_{sd}=(P_{LT}-P_a)(A_d/A_s), \quad (EQ. 6)$$

where, $P_{LT}$ is the dynamic pressure near the leaking duct (on the entry to the subglottis), $P_a$ is the ambient pressure, $A_d$ is the cross sectional area of the leaking duct (on the entry to the subglottis) and $A_s$ is the cross sectional area of the subglottis at the pressure measuring location.

As a representative numerical example, when the diameter of the trachea is about 15-30 mm, the inner diameter of the endotracheal duct is about 7-8.5 mm and the cross sectional area of the leaking duct is about 5-25 mm$^2$, $P_{sd}$ is from about 0.01 to about 2 mm Hg. Thus, according to a preferred embodiment of the present invention the pressure measuring device is characterized by a dynamic range of about 0-2 mm Hg and resolution of 0.01 mm Hg.

Miniature sensitive pressure measuring devices are known in the art. Representative example of suitable pressure measuring devices include the pressure sensors of Nexense™, Israel, described, e.g., in U.S. Pat. Nos. 6,621, 278 and 6,856,141, International Publication Nos. WO 00/67013, WO 03/036321, WO 03/048688, WO 2004/072658, WO 2005/062719, and WO2005/076727, and U.S. Patent Application Nos. 20050027206, 20040207409, 20040104733, and 20020105340, the contents of which are hereby incorporated by reference.

In an additional embodiment, the leakage-indicating measure comprises flow data being indicative of fluid flow near the cuff outside endotracheal tube. Flow data can be measured using a flow measuring device, such as a flow meter. The flow measuring device is preferably located near the cuff within the subglottis, such that when air flows from the lungs through the leakage duct, the flow measuring device measures the flow. According to a preferred embodiment of the present invention the flow measuring device is characterized by a dynamic range of about 1-3 m/s and resolution of about 10%. Miniature sensitive flow measuring devices are manufactured by Nexense™, Israel, and described in the aforementioned patents and patent applications.

In still another embodiment, the leakage-indicating measure comprises optical data being indicative of presence of secretions near the cuff outside endotracheal tube. In this embodiment, the measuring device comprises one or more miniature cameras located below the cuff, between the cuff and the lung. The cameras capture images, preferably video images, which can be analyzed to identify leakage of secretions through the leaking duct in the direction of the lungs. Mature cameras which can be mounted on an endotracheal tube are known in the art, (see, e.g., MedGadget Journal, March 2005 issue, http://www.medgadget.com/archives/2005/03/etview_ett.html)

In yet another embodiment, the leakage-indicating measure comprises difference between inhaled and exhaled air volumes passing through the endotracheal tube. In this embodiment, the measurement can be performed at the inlet of the breathing machine. The amount of inhaled and exhaled air volume is recorded and the difference therebetween is calculated. Based on this difference, the identification of leakage is achieved.

In a further embodiment, the leakage-indicating measure comprises electrical characteristics of fluid above the cuff outside endotracheal tube. In this embodiment, the fluid above the cuff is transferred into a chamber where it is being heated. When the air contains $CO_2$ it becomes electrically conductive at high temperatures. The electrical conductivity thus serves as a proxy measure to the concentration of $CO_2$ above the cuff. According to a preferred embodiment of the present invention a leakage is identified whenever the electrical conductivity of the air above the cuff exceeds an optimal level. The optimal level can correspond to the aforementioned partial $CO_2$ pressure levels.

Figure 7A:
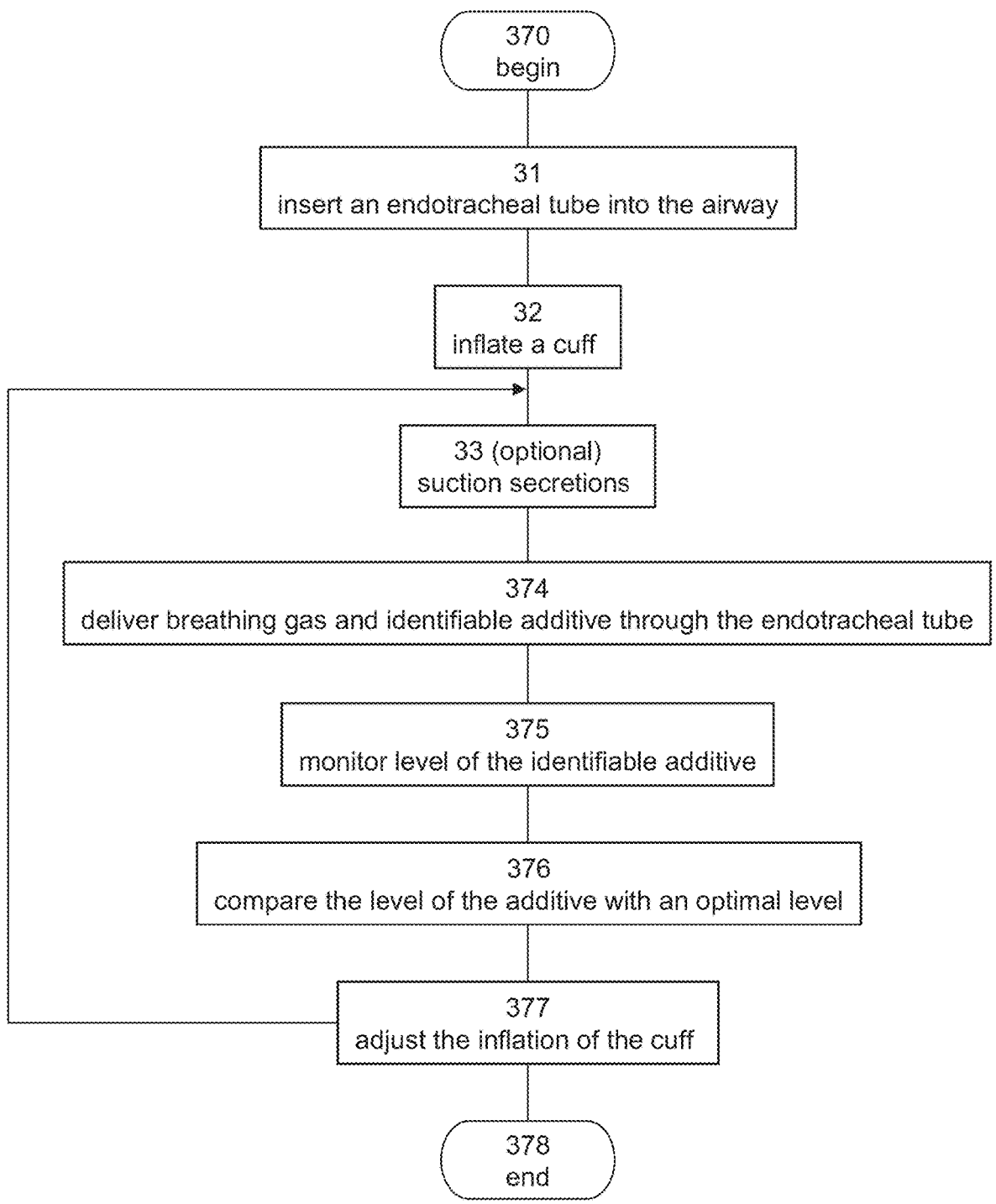
FIGS. 7a-c are flowchart diagrams of another method suitable for intubating a subject, according to various exemplary embodiments of the present invention.
Figure 7B:
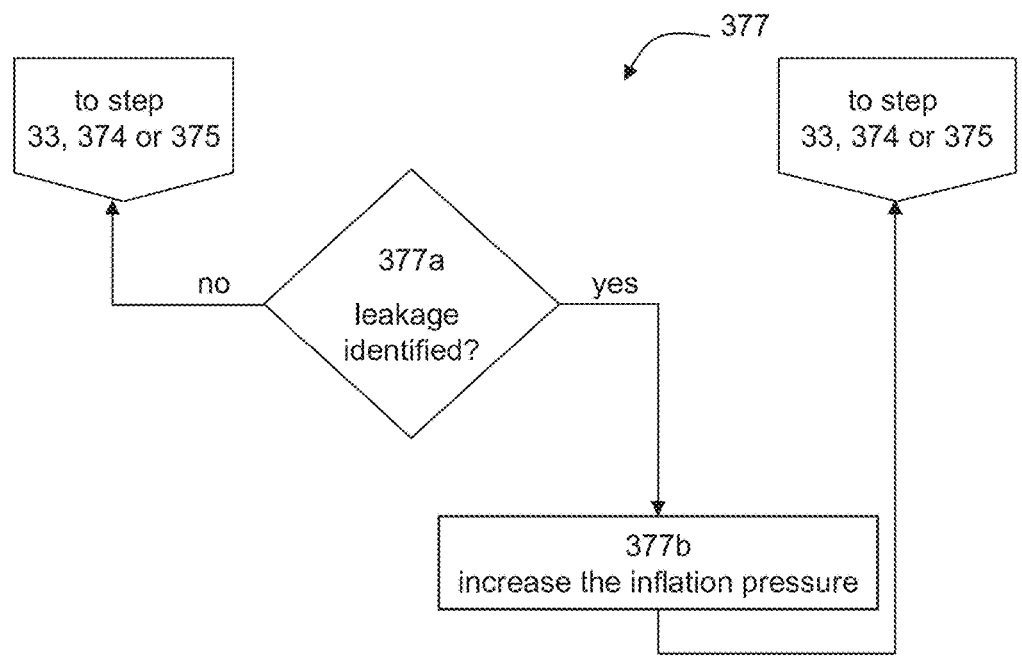
Figure 7C:
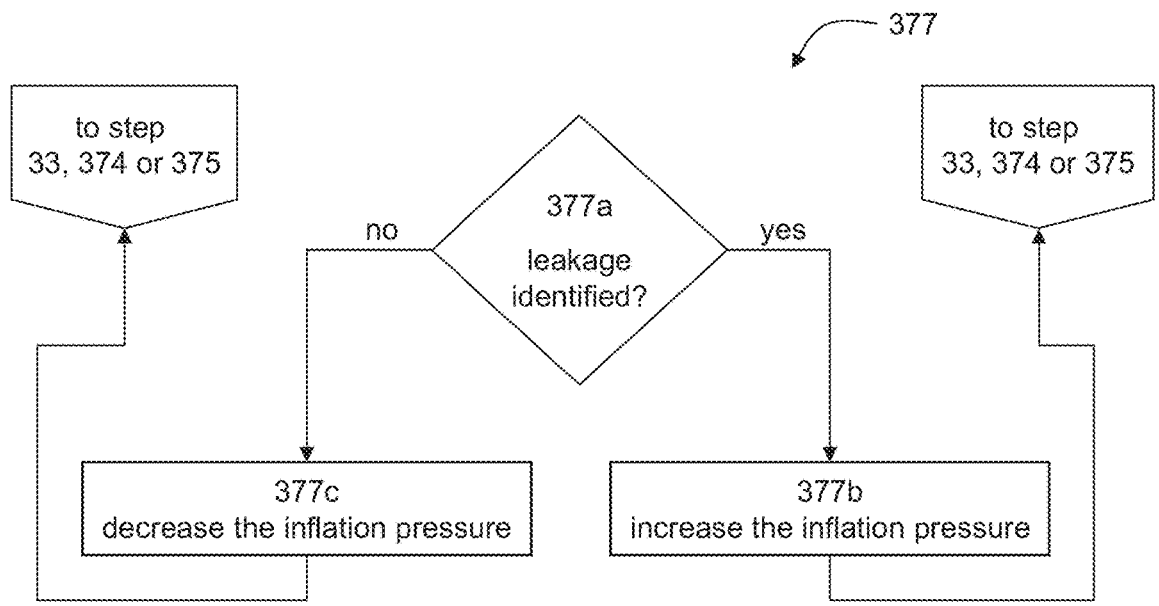

Reference is now made to FIGS. 7a-c which are flowchart diagrams of a method suitable intubating a subject, in preferred embodiments in which the leakage is identified by delivering additives to the subject.

The method begins at step 370 and continues to steps 31 and 32 as described hereinabove. The method can also continue to the optional suctioning step 33 as described hereinabove. The optional suctioning step can be performed in an intermittent, continuous or contemporaneous manner with any of the other method steps described below. More specifically, step 33 can be performed in a continuous manner contemporaneously with a sequential execution of steps 374-377 or 375-377 described below. Alternatively, step 33 can be executed whenever the method loops back from step 377.

The method continues to step 374 in which a breathing gas and one or more identifiable additives are delivered through the endotracheal tube. The breathing gas can be any breathing gas typically delivered to subjects from a conventional breathing or anesthesia machine, such as, but not limited to, air, filtered air, enriched air, a mixture of air and one or more anesthetic agents, and the like. The identifiable additive is preferably in fluid form (e.g., gaseous form) and it can be either mixed with the breathing gas prior to the delivery or it can be delivered from a different container. Being designed to enter the body of the subject, the identifiable additive is preferably of low toxicity or, more preferably non toxic.

The delivery of the additive is preferably performed so as to allow the additive to enter the lungs of the subject. During the breathing cycle, additive remnants pass through the lungs and, together with the carbon dioxide waste, are expelled from the lungs by the breathing machine. Alternatively, the additive can be delivered to a location above the cuff, between the airway's wall and the endotracheal tube. In this embodiment, the additive only enters the lungs when there is a leaking duct between the cuff and the airway.

The delivery of the additive can be performed continuously throughout the procedure or at predetermined time intervals (e.g., whenever the method loops back to step 33 or step 374, as further detailed hereinafter). In the embodiment in which the additive is delivered to a location above the cuff, the delivery can be executed once for the entire procedure, or whenever the level of the additive at the location above the cuff decreases to below a predetermined threshold.

Many types of identifiable additives are contemplated. Broadly speaking, for the additive to be identifiable, it should have at least one measurable property which can be used for distinguishing the additive from the breathing gas or other materials in the environment. Thus, the additive is preferably absent from the environment or present in environment in low and known concentrations. When the additive is already present in the environment, it is preferably delivered at a sufficiently higher concentration so as to allow identifying the additive by its concentration level. The distinguishing property of the additive can be, for example, atomic mass, molecular mass and/or one or more other distinguishable properties, including optical, fluorescent and radiative properties. Additionally or alternatively, the additive can have specific electric and/or magnetic properties which can be used to identify the additive.

Representative examples of identifiable additives suitable for the present embodiments include, without limitation, inert gases such as helium, krypton, etc.; radioisotopes, preferably low-radiation radioisotopes with sufficiently short half lives (several seconds to several days) such as technetium radioisotope (e.g., Tc-99), xenon radioisotope (e.g., Xe-133), krypton radioisotope (e.g., Kr-81); colored gases, preferably non-toxic colored gases; and various fluorescent materials, preferably non-toxic fluorescent materials.

The amount of additive which is delivered is preferably selected sufficiently high to allow its identification and sufficiently low so as not to interfere with the breathing of the subject or cause damage to living tissue. The amount can be selected in accordance with the FDA regulations of the specific type of additive used. The optimal amount thus depends on the type of additive and the measuring device which identifies it. It was found by the present inventors that additives suitable for the present embodiments can be identified with an accuracy of from about $7.5 \times 10^{-12}$ (e.g., via mass spectrometry) to about 0.001 (e.g., via radiation detection). Thus, the ratio between the volume of additive to the volume of inhaled air is preferably less than R, where R is a number from about $7.5 \times 10^{-12}$ to about 0.001. Where the lower limit is applicable to detection via mass spectrometry.

As used herein, "about" refers to ±10% (e.g., "about $7.5 \times 10^{-12}$" refers to the range $6.75 \times 10^{-12}$-$8.25 \times 10^{-12}$, while "about 0.001" refers to the range 0.0009-0.0011).

The method continues to step 375 in which the level of the identifiable additive is monitored. The monitoring is performed so as to identify leakage of the additive past the cuff towards the vocal cords. As will be appreciated by one of ordinary skill in the art, the identification of such leakage is a proxy to the formation of a leaking duct between the cuff and the airway's inner wall, which formation is typically accompanied by secretions past cuff to the lungs.

In various exemplary embodiments of the invention the monitoring is performed in a substantially continuous manner throughout the intubating procedure. This can be done, for example, by obtaining a series of real-time values for the level of the additive. In the embodiments in which more than one additive is delivered through the endotracheal tube, the monitoring preferably comprises measurements for more the level of more than one additive, more preferably all the delivered additives. In this case, all the measures are preferably weighted using a predetermined set of weights which may correspond, for example, to the relative accuracy level of each measurement and/or its correlation level with the secretions leakage.

The monitoring can be performed using one or more measuring devices suitable for measuring the distinguishing property of the additive. According to a preferred embodiment of the present invention the insertion of the endotracheal tube is accompanied by the insertion of a communication device (e.g., a conduit) which communicates with the measuring device(s). The conduit can be disposed externally to the endotracheal tube or it can be embedded in the wall of the tube, as further detailed hereinafter.

The monitoring is performed at a monitoring location which is accessible to the measuring device or the communication device. In various exemplary embodiments of the invention the monitoring is done by sampling fluids (gas or liquid) from the monitoring location and delivering the sample to the measuring device for analysis. Preferably, the monitoring location is selected so as to optimize the accuracy of the measurement while minimizing discomfort to the subject. Suitable monitoring locations include, without limitation, above the cuff between the endotracheal tube and the walls of the airway, at the nostril of the subject or above the vocal cords (e.g., at the oropharynx) and/or below cuff and adjacent thereto. Whereas the nostril or oropharynx are more convenient measurement locations to the operator and patient, performing the measuring near the cuff is more preferred from the standpoint of the measurement accuracy and analysis reliability. When the additive is delivered to a location above the cuff, the monitoring location can be below the cuff, in the lungs, or in the breathing lumen of the endotracheal tube near or at the ventilator.

According to a preferred embodiment of the present invention the measurements are performed by a mass spectrometer or a gas analyzer, which can provide information regarding the composition and abundance of the atoms present between the airway's wall and the endotracheal tube, thereby to identify additive and to measure its level. For example, when the additive comprises an inert gas (e.g., helium, krypton) the mass spectrometer can identify presence of the atoms of the inert gas (e.g., He, Kr) and optionally measure their concentration level. Other gaseous materials can also be identified using mass spectrometer.

In another embodiment, the measurements are performed by a radiation detecting device. This embodiment is preferred when the additive has specific radiative properties. For example, when the additive comprises radioisotope (e.g., Tc-99, Xe-133, Kr-81), the radiation detecting device can detect radiation emitted by the radioisotope and the presence and/or concentration level of the radioisotope in the between the airway's wall and the endotracheal tube can thus be determined. This can be achieved by sampling fluids (gas or liquid) from the monitoring location and delivering the sample to the radiation detecting device.

An additional embodiment is preferred when the additive has a distinguishing optical property. In this embodiment the measurements are performed by an optical device capable of measuring the optical property. For example, the optical property of the additive can be a distinct color (such as, for example, in the case of colored gas), in which case the optical device can include a miniature camera or an optical waveguide coupled to an external camera. Miniature cameras mountable on an endotracheal tube are known in the art, (see, e.g., MedGadget Journal, March 2005 issue, http://www.medgadget.com/archives/2005/03/etview_ett.html).

Images captured by the camera can be processed to detect the presence of the additive and optionally determine its concentration level above the cuff. The optical property of the additive can also be fluorescence, in which case the optical device can be a fluorescence camera for detecting fluorescent emissions from the additive, thereby enabling the presence detection and/or concentration level measurement of the additive. When the additive is delivered to a location above the cuff, images are preferably captured below the cuff so as to identify leakage once the additive passes the cuff downstream to the lungs. In this embodiment, the additive can also be selected such that its passing through the leaking duct is accompanied by the formation of colored or colorless bubbles which can be detected by the camera. Bubbles can be also detected by a miniature ultrasound device.

An additional embodiment is preferred when the additive has a distinguishing electrical property. In this embodiment the measurements are performed by a device capable of measuring electrical properties, such as conduction or resistance. Alternatively or additionally, when the additive has a distinguishing magnetic property, the measurements are performed by a device capable of measuring magnetic properties, e.g., magnetization. Thus, measurements of the respective quantity can be performed substantially continuously in the monitoring location so as to determine presence or concentration level of the additive above the cuff.

Once the measurements are performed the method preferably continues to step 376 in which the level of the identifiable additive is compared with an optimal level thereof, which is preferably predetermined. In the preferred embodiment in which more than one additive is used, the level of each identifiable additive is preferably compared with a respective optimal level.

The optimal level is preferably the maximal level of the respective additive which is indicative to a negligibly low or no leakage of secretions from above the cuff into the lung. Thus, the optimal level enacts a leakage identification threshold. As long as the level of the additive is below the threshold, the leakage is considered negligible (or nonexistent) and the airway is considered properly sealed. The threshold is typically a lower bound, so that secretions leakage is identified at the location of the cuff whenever the level of the additive exceeds the threshold.

The optimal level can be an absolute optimal level or it can be defined relative to an online reference of, e.g., ambient or breathing gas. The optimal level can be extracted from studies directed to determine this level, tables, charts, graphs or formulae obtained by empirical considerations and/or theoretical calculations.

According to a preferred embodiment of the present invention the method proceeds to step 377 in which the inflation of the cuff is adjusted, based on the level of the identifiable additive. The adjustment is performed in a manner such that both leakage of secretion and occurrences of pressure associated damages are generally minimized. From step 377 the method, optionally and preferably, loops back to step 33, 374 or 375.

Two alternative and optional execution procedures for step 377 are illustrated in the partial flowcharts of FIGS. 7b-c. Hence, from step 376 (not shown, see FIG. 7a) the method continues to decision step 377a in which the method decides whether or not a non-negligible leakage is identified, based, as stated on the level of the additive. If non-negligible leakage is identified the method continues to process step 377b in which the inflation pressure of the cuff is increased so as to provide better sealing. If the method decides that there is no leakage (or that the leakage is negligible), the method can either loop back to step 373, 374 or 375 without changing the inflation pressure (FIG. 7b), or proceed to step 377c in which the inflation pressure of the cuff is decreased (FIG. 7c). From step 377c the method preferably loops back to step 373, 374 or 375. The advantage of the embodiment of FIG. 7c is that it allows further optimization of the inflation pressure in the cuff. The inflation pressure in the cuff can be decreased as long as the leakage is sufficiently low or there is no leakage.

Thus, the method of the present embodiment provides a closed loop control on the inflation of the cuff, such that leakage of secretions is minimized or substantially prevented with a minimal local pressure on the trachea. Such control facilitates an efficient breathing assistance to the subject with minimal risk to lung infections or pressure related damage to the airway's wall.

The method ends at step 378.

Figure 8:
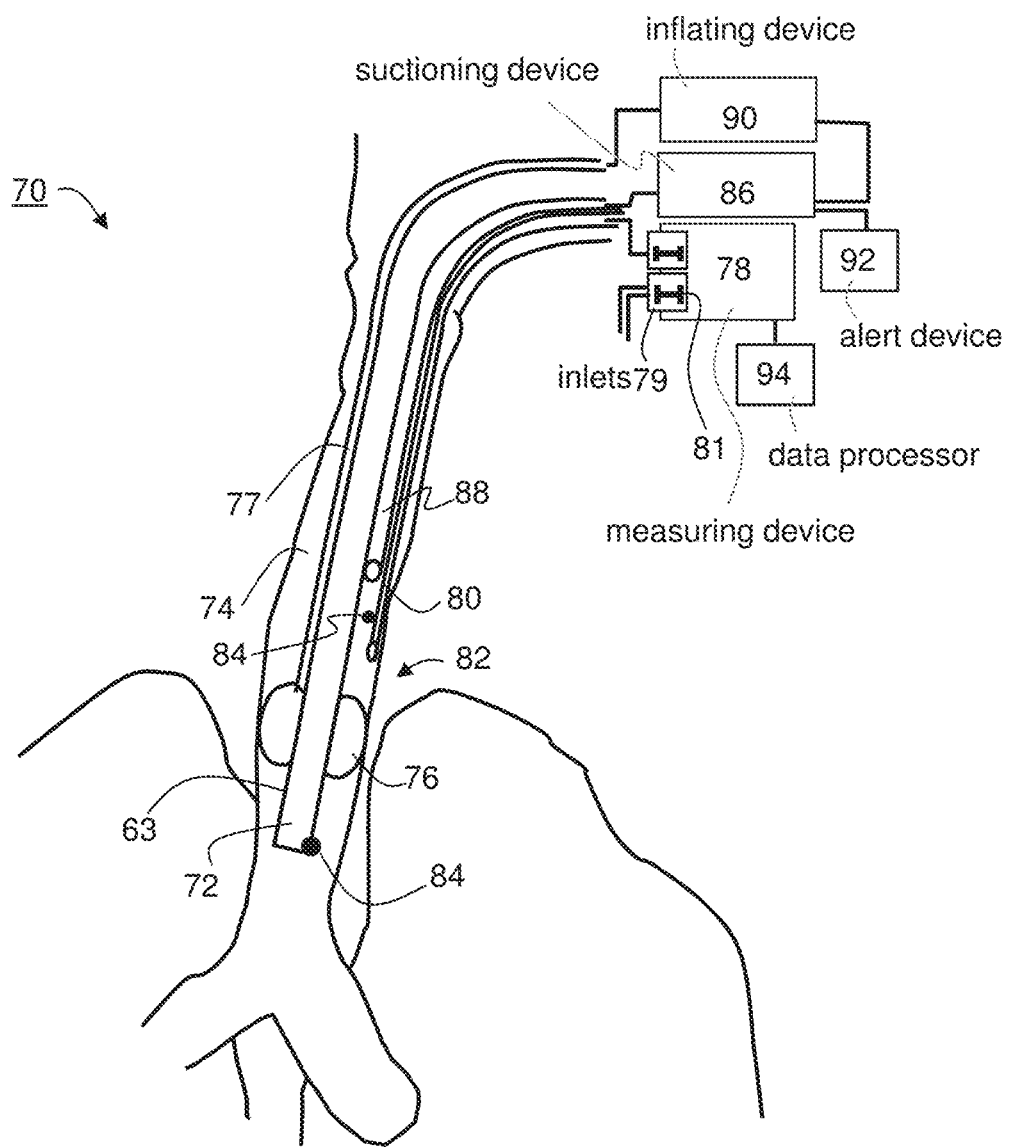
FIG. 8 is a simplified illustration of a system for intubating a subject, according to various exemplary embodiments of the present invention.

Reference is now made to FIG. 8 which is a simplified illustration of a system 70 for intubating a subject, according to various exemplary embodiments of the present invention. System 70 comprises an endotracheal tube 72, adapted to be inserted into the airway 74. Endotracheal tube 72 is associated with a cuff 76 capable of being inflated, for example, via an inflation conduit 77 below the vocal cords of the subject (not shown, see, e.g., FIGS. 4a and 6a). System 70 further comprises a measuring device 78, for measuring at least one measure which is indicative of secretion leakage as further detailed hereinabove. In various exemplary embodiments of the invention device 78 performs measurements to measures directly related to $CO_2$ (concentration, partial pressure) or proxy measures to $CO_2$. It is expected that during the life of this patent many relevant measuring devices suitable for measuring proxy measures to $CO_2$ will be developed and the scope of the term measuring devices is intended to include all such new technologies a priori.

Device 78 can be, for example, a $CO_2$ concentration measuring device, a $CO_2$ partial pressure measuring device, an acoustic measuring device, a pressure measuring device, a flow measuring device, an optical measuring device (e.g., a camera), a gas-volume measuring device, an electrical characteristics measuring device.

In the embodiments in which ambient $CO_2$ partial pressure is measured, device 78 is preferably capable of performing two parallel measurements, for example, using two or more separate inlets 79 and an arrangement of unidirectional valves 81. Inlet 79 can also be used for measuring ambient measure (e.g., $CO_2$ partial pressure) to be used as a reference measure.

Device 78 can comprise, or be associated with a data processing unit 94 which process or analyze the data corresponding to the measured quantities. For example, can convert the measured quantities to digital data and transfer the data to unit 94 for further processing, such as, but not limited to, the analysis of data corresponding to acoustical measurements (e.g., filtration of background data or calculation of $\Delta f$, $\Delta t$ or $v_L$, as further detailed hereinabove) or the analysis of data corresponding to optical measurements. Unit 94 can also perform comparison, preferably in real-time, between the level of the measure and its corresponding optimal value. For example, in various exemplary embodiments of the invention, unit 94 performs real-time comparison between the $CO_2$ partial pressure near the cuff and the ambient $CO_2$ partial pressure.

Depending on the type of the measuring device, the device can be located at the desired measuring location 82, or more preferably it can communicate with the measuring location, for example, using a measuring conduit 80. It is to be understood that although FIG. 8 shows measuring location 82 above cuff 76, this need not necessarily be the case, since, as stated, it may not be necessary for the measuring location to be above the cuff, as further detailed hereinabove.

Device 78 can also comprise one or more sensors 84 located at the measuring location and configured to communicate with device 78 via a communication channel, such as, but not limited to, measuring conduit 80, which can be or include a suitable transmission line. The type of sensors depends on the type of the measuring device. For example, when the measuring device is an acoustical measuring device, the sensors are acoustical sensors, when the measuring device is a pressure measuring device the sensors are pressure sensors and the like.

According to a preferred embodiment of the present invention system 70 comprises a suctioning device 86 for suctioning secretions at a suctioning location 87 in the airway above cuff 76. Suctioning device 86 can be in fluid communication with suctioning location 87 either by a suctioning conduit 88, extending from device 86 to location 87, or by conduit 80, in which case conduit 80 serves as a suctioning and measuring conduit. Conduit 80 and/or conduit 88 can be disposed either internally within the endotracheal tube or externally thereto, as desired. Conduits 80 and/or 88 can also be embedded in wall 63 of tube 72.

In various exemplary embodiments of the invention system 70 comprises an inflating device 90 for adjusting the inflation of cuff 76 based on signals received from device 78. This can be done either manually, by the operator, in which case the measuring device comprises a display device for displaying the level of the measure, or automatically, in which case the inflating device is in communication with the measuring device, thereby forming therewith a closed loop control.

System 70 can also comprise an alerting unit 92 which communicates with measuring device 78. Unit 92 serves for producing an alert when the level of the measure exceeds the optimal level.

Figure 9A:
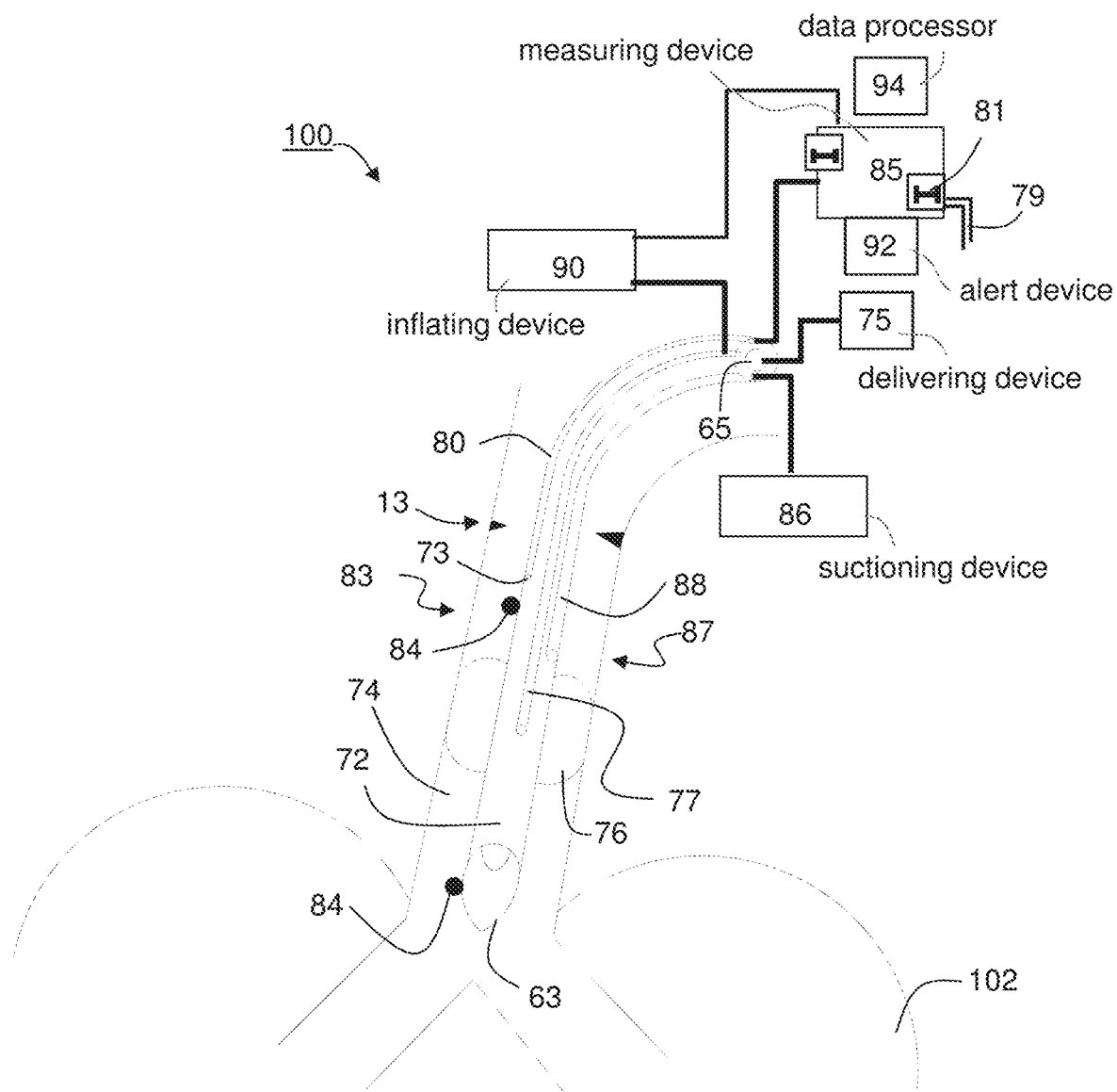
FIGS. 9a-b are simplified illustrations of another system for intubating a subject, according to various exemplary embodiments of the present invention.
Figure 9B:
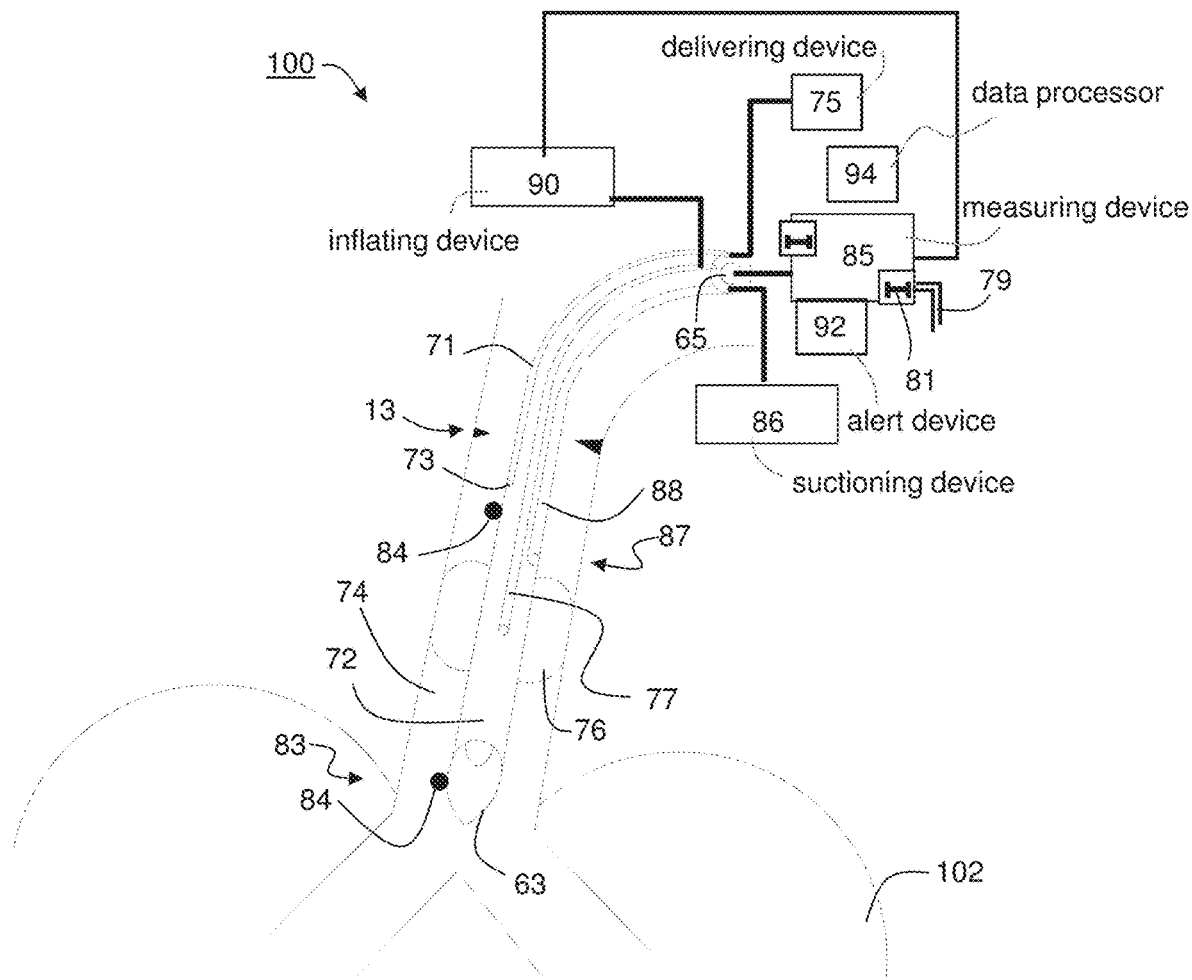

Reference is now made to FIGS. 9a-b which is a simplified illustration of a system 100 for intubating a subject, according to various exemplary embodiments of the present invention. Similarly to system 70 above, system 100 preferably comprises endotracheal tube 72, cuff 76 and inflation conduit 77 as further detailed hereinabove. In various exemplary embodiments of the invention system 100 further comprises an additive delivering unit 75 which delivers one or more identifiable additive(s) through the endotracheal tube, as further detailed hereinabove. Unit 75 is thus operatively associated with tube 72. This association can be via the breathing or anesthesia machine (not shown), in which case unit 75 is preferably a part of, or being in fluid communication with, the machine such that the additive is mixed with the breathing gas prior to the delivery of the additive through tube 72.

Alternatively, unit 75 can be a fluid communication with tube 72, in which case the additive is delivered directly from unit 75 to tube 72. When it is desired to allow the additive to enter the lungs 102 of the subject, the additive and the breathing gas are preferably delivered through the breathing lumen 65 of tube 72. In this embodiment, the additive and the breathing gas can be allowed to mix. When it is desired to deliver the additive to a location above the cuff, the additive is preferably delivered through an additive delivery conduit 71 which can include an opening 73 above cuff 76 (see FIG. 9b). Conduit 71 can be disposed within the lumen 65 of tube 72 or being adjacent thereto. Conduit 71 can also be embedded in the wall 63 of tube 72. Preferably, but not obligatorily, lumen 65 and conduit 71 are devoid fluid communications thereamongst. Also contemplated are asymmetrical configurations employing unidirectional valves, in which the additive is prevented from entering lumen 65 but the breathing gas is allowed to enter conduit 71 or vise versa. In the embodiments in which the additive is delivered through lumen 65, conduit 71 can be used as a measuring conduit 80, as further detailed hereinbelow.

System 100 further comprises a measuring device 85, for measuring the level of the identifiable additive(s) as further detailed hereinabove. Device 85 preferably communicates with a monitoring location 83 which, as stated, can be above the cuff, at the nostril of the subject or above the vocal cords (e.g., at the oropharynx) and/or below the cuff and adjacent thereto. In the embodiment shown in FIG. 9a monitoring location 83 is above the cuff between the endotracheal tube and the walls of the airway.

Device 85 can measure one or more of the aforementioned distinguishing properties of the additive. Thus, device 85 can be, for example, a mass spectrometer, a gas analyzer, an optical measuring device (e.g., an optical camera or a fluorescence camera), a miniature ultrasound device, electrical characteristics measuring device (e.g., a conduction measuring device, a resistance measuring device) and a magnetic characteristics measuring device (e.g., magnetization measuring device). Device 85 can also be a combination of several devices, each designed and constructed to measure a different quantity. For example, device 85 can include a mass spectrometer and a camera or any other combination.

Device 85 is preferably capable of performing two parallel measurements, for example, using two or more separate inlets 79 and an arrangement of unidirectional valves 81. This embodiment is particularly useful when it is desired to determine the level of the additive in the environment, for example for comparing the level of the additive at the monitoring location with the environmental level.

Device 85 can comprise, or be associated with data processing unit 94 which processes or analyzes the data corresponding to the measured quantities, as described above. The principles and operations of data processing unit 94 of system 100 are similar, mutatis mutandis, to the principles and operations of data processing unit 94 of system 70. For example, device 85 can convert the measured quantities to digital data and transfer the data to unit 94 for further processing, such as, but not limited to, the analysis of data corresponding to optical measurements.

Device 85 can be located at the desired monitoring location 83, or it can communicate with monitoring location 83, for example, using measuring conduit 80. It is to be understood that although FIG. 9*a* illustrates monitoring location 83 above cuff 76, this need not necessarily be the case, since, as stated, many other monitoring locations are contemplated. When the additive is delivered to a location above the cuff, device 85 can sample gas directly from lumen 65 to determine presence of the additive therein.

In the exemplified illustration of FIG. 9*a*, the additive is delivered through lumen 65 and device 85 communicates with location 83 via conduit 80, and in the exemplified illustration of FIG. 9*b*, the additive is delivered through conduit 71 and device 85 communicates with lumen 65, either directly or indirectly, e.g., through the breathing machine or the ventilator. It is to be understood that although FIG. 9*b* illustrates monitoring location 83 in or near the lungs, this need not necessarily be the case, since many other monitoring locations are contemplated as further detailed hereinabove.

Device 85 can also comprise one or more sensors 84 located at the monitoring location and configured to communicate with device 85 via a communication channel, such as, but not limited to, measuring conduit 80, which can be or include a suitable transmission line. The type of sensors depends on the type of the measuring device.

System 100 can also comprise other components, such as, but not limited to, suctioning device 86, suctioning conduit 88, inflating device 90 and alerting unit 92, as further detailed hereinabove.

Additional objects, advantages and novel features of the present invention will become apparent to one ordinarily skilled in the art upon examination of the following example, which are not intended to be limiting. Additionally, each of the various embodiments and aspects of the present invention as delineated hereinabove and as claimed in the claims section below finds experimental support in the following example.

EXAMPLE

Reference is now made to the following examples, which together with the above descriptions illustrate the invention in a non limiting fashion.

In the present example, continuous assessment of leakage near the endotracheal tube cuff by monitoring $CO_2$ pressure ($PCO_2$) in the upper airway, in accordance with the teachings of the present embodiments.

The purpose of this study was to establish an accurate, objective, non-invasive bedside method for assessment of a leakage near the endotracheal tube cuff. Initially, the feasibility of the method was investigated in a human simulator. Subsequently, leaks at various cuff pressures were evaluated by iodine leakage test in a porcine models simulating human airway mucosa. Finally, the feasibility of the method was evaluated in 60 patients undergoing elective surgery, comparing the new method to the standard clinical evaluation used today.

Methods

Three anatomical locations were evaluated, in accordance with various exemplary embodiments of the present invention: (i) between the endotracheal tube cuff and the vocal cords through a suction mini-guide lumen catheter attached externally to the endotracheal tube; (ii) at the oropharynx above the epiglottis by a catheter inserted through a plastic oropharyngeal airway; and (iii) in the nostrils through a nasal cannula.

Figure 10:
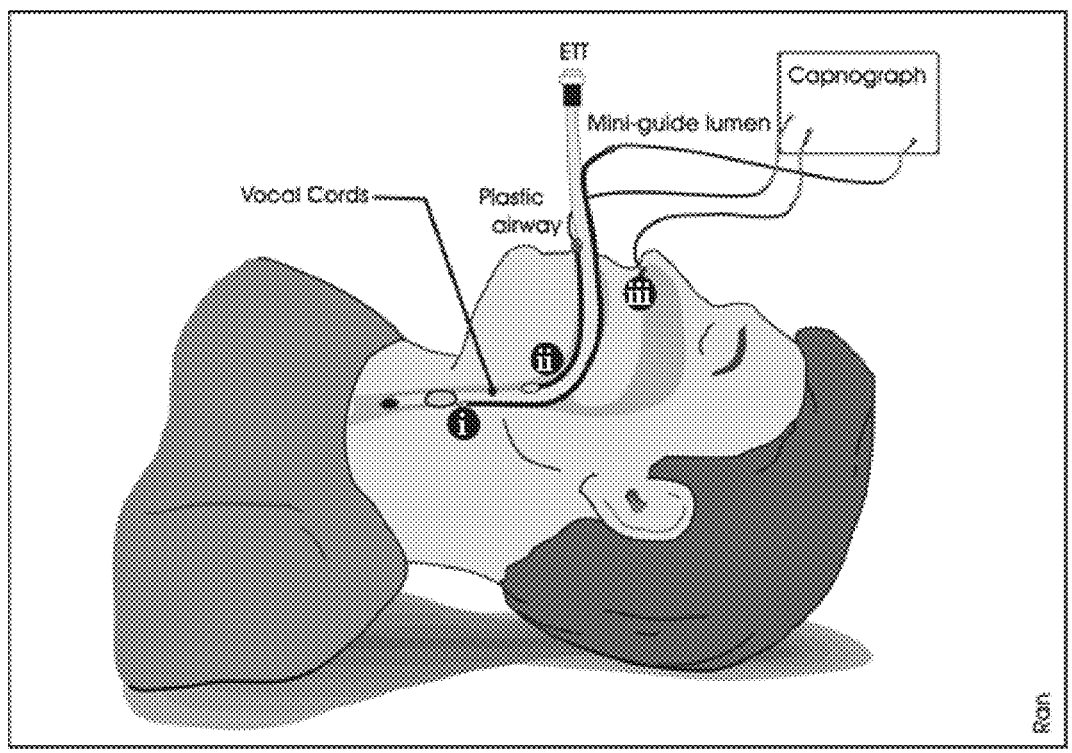
FIG. 10 shows the anatomic locations of $CO_2$ sampling performed according to the teaching of the present invention, in a human simulator and in patients under general anesthesia.

FIG. 10 shows the anatomic locations of $CO_2$ sampling in the human simulator and in patients under general anesthesia.

The study was performed in 3 phases. In phase 1 the feasibility of the method in a human simulator was ascertained. In phase 2, the method in a porcine model was experimentally explored. In phase 3 the method was compared with the standard technique for estimating optimal endotracheal tube cuff filling in 60 surgical patients under general anesthesia.

Throughout the three phases of the study, $PCO_2$ levels were recorded using a micro-side-stream capnograph (Microcap®, Oridion, Jerusalem, Israel) with flow rate of 50 ml/min-7.5+15 ml/min and rise time to CO2 step of about 0.2 s. The Microcap® utilizes an algorithm which detects and saves only the end tidal $PCO_2$ values. In order to avoid inaccurate processing of $PCO_2$ data by the capnograph, the routinely utilized algorithm to detect end tidal $PCO_2$ was neutralized and all $PCO_2$ values were directly transported and saved on a data processor. Any increase of more than 1 mm Hg in $PCO_2$ reading was interpreted as a sign of leakage around the cuff and the appropriate cuff pressure was set accordingly. This cuff pressure was automatically kept constant by a special electronic cuff pressure controller device (TRACOE® cuff pressure controller, Germany) with controlled accuracy of ±2 mbar, avoiding possible cuff pressure changes due to fluctuations in inspiratory pressures or any other local variables. Endotracheal tubes with high volume, low pressure cuffs having an external side attached mini-guide lumen which opens 1 cm above the cuff (Hi-Lo® Evac, Mallinckrodt, USA) were used. The proximal end of the suction mini-guide was connected to the capnograph (see FIG. 10).

Figure 11:
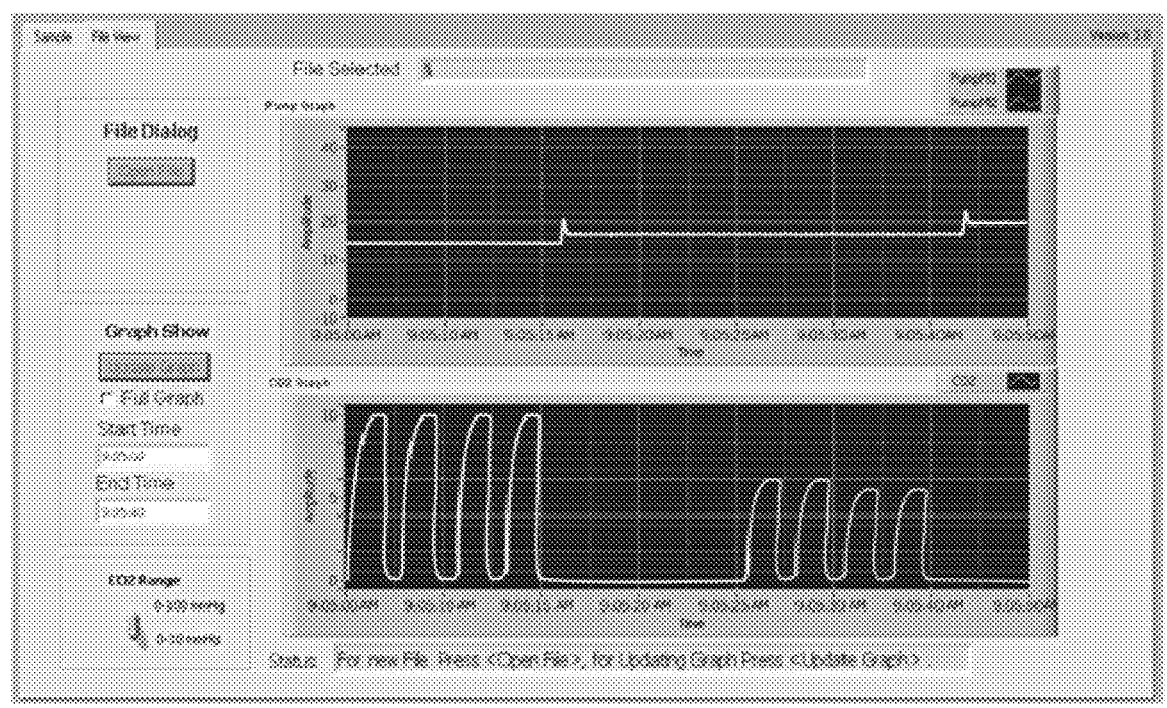
FIG. 11 shows exhaled $CO_2$ pressure waveform in accordance with endotracheal tube cuff pressures as displayed during an experiment performed according to the teaching of the present invention.

FIG. 11 shows the exhaled $CO_2$ pressure waveform in accordance with endotracheal tube cuff pressures as displayed during the first phase. The suction time (from the upper airways) is represented by the straight line of the $CO_2$ pressure waveform.

Phase 1—Human Simulator Model

A human simulator of a 70 kg man (Medical Education Technologies, Inc (METI) Sarasota, Fla.) was used. A Hi-Lo® Evac endotracheal tube No. 8 was inserted into the human simulator trachea. The tracheal diameter at the location of the endotracheal tube cuff was 25 mm. Exhaled air end-tidal $CO_2$ of 40 mm Hg was simulated by adjusting a continuous $CO_2$ stream into the simulator lungs.

While ventilating the human simulator the cuff was sequentially inflated, 2 mm Hg at a time, and $PCO_2$ leakage level was measured at the three anatomic sites (see FIG. 10). After each cuff pressure change the oropharynx was suctioned to prevent $CO_2$ remnants from altering subsequent measurements.

Phase 2—Porcine Model

Experiments were conducted according to the National Institute of Health Guidelines for the Care and Use of Laboratory Animals. Two pigs, weight 10 kg and 13 kg, underwent general anesthesia with a No. 7 endotracheal tube. $CO_2$ leakage was assessed by a 4 mm diameter catheter inserted directly through a small incision into the trachea 1 cm above the endotracheal tube cuff and below the vocal cords. The endotracheal tube cuff pressure was increased sequentially, 2 mm Hg at a time, and $PCO_2$ was measured through the catheter. After each measurement the upper airway was suctioned so as to avoid any $CO_2$ remnants.

After reaching a steady cuff pressure with no $PCO_2$ readings at the upper airway, a tracheal "window" was surgically opened below the endotracheal tube cuff. Iodine solution (5 cc) was injected above the cuff and rested there for 60 minutes while iodine leakage below the cuff was evaluated through the tracheal "window" at different cuff pressure levels. Throughout the experiment (including the period of iodine leakage measurements) animals were maintained on the same positive pressure ventilation and the endotracheal tube location and animal head and neck position were not changed.

Phase 3—Human Subjects

Sixty consecutive adult patients undergoing elective surgery with balanced generalized anesthesia ($NO_2$:$O_2$) were included in the study. Patients with history of cigarette smoking or dyspnea were preassessed by pulmonary function tests, so as to obtain a homogenous group of patients regarding to mechanical ventilation volumes and pressures. Nine patients were excluded due to forced expiratory volume per second ($FEV_1$) or vital capacity less than 50% of predicted. The study protocol was approved by the local ethics committee and patients signed an informed consent.

In all patients the intubation was performed by an anesthesiologist and the endotracheal tube position inside the trachea was determined according to the height of the patient using the following formula: the length from the distal tip of the endotracheal tube to the right mouth angle (measured in cm)=[body height (in cm)/5]−13 [Cherng C H, Wong C S, Hsu C H, Ho S T. Airway length in adults: estimation of the optimal endotracheal tube length for orotracheal intubation. *J Clin Anesth*. 2002; 14: 271-274].

After intubation, the anesthesiologist was requested to set the minimal endotracheal tube cuff pressure required to prevent leakage according to exhalation-inhalation volume difference and air leakage heard with the stethoscope around the cuff. The cuff pressure was considered optimal by the anesthesiologist when there was no exhalation-inhalation volume difference and no air leakage heard with the stethoscope using the minimal cuff pressure for 5 minutes. Once cuff pressure level was considered optimal by the anesthesiologist, the $PCO_2$ was measuring at the aforementioned 3 locations.

Based on the findings in the porcine model, optimal cuff filling was defined as the minimal cuff pressure required for avoiding a $PCO_2$ leakage of more than 2 mm Hg proximal to the endotracheal tube cuff via the external mini-guide lumen of the Hi-Lo® Evac endotracheal tube. Suction was performed through the plastic airway as needed and 2 minutes before each $PCO_2$ measurement. Continuous monitoring of $PCO_2$ from the 3 anatomic locations was performed throughout the operation.

Statistics

Statistical SPSS™ software (version 10.0, SPSS Inc., Chicago, Ill.) was used for all analyses performed. Categorical data are expressed in numbers and percentages forms. Continuous data are expressed as means±standard deviations and compared by a paired t-test. Regression coefficient (R) was calculated as a measurement of correlation between endotracheal tube cuff pressure and $PCO_2$ in the upper airways and expressed as $R^2$. P values below 0.05 were considered significant.

Results

Phase 1—Human Simulator Model

FIG. 11 illustrates an example of the exhaled $PCO_2$ waveform in accordance with endotracheal tube cuff pressure as displayed on a PC monitor in the human simulator model. A linear correlation was observed between the endotracheal tube cuff pressure and the $PCO_2$ measured above the cuff in all three anatomic locations: (i) between the cuff and the vocal cords, $R^2$=0.954, p<0.0001; (ii) at the oropharynx above the epiglottis, $R^2$=0.923, p<0.0001; (iii) at the nostrils, $R^2$=0.911, p<0.0001.

Figure 12:
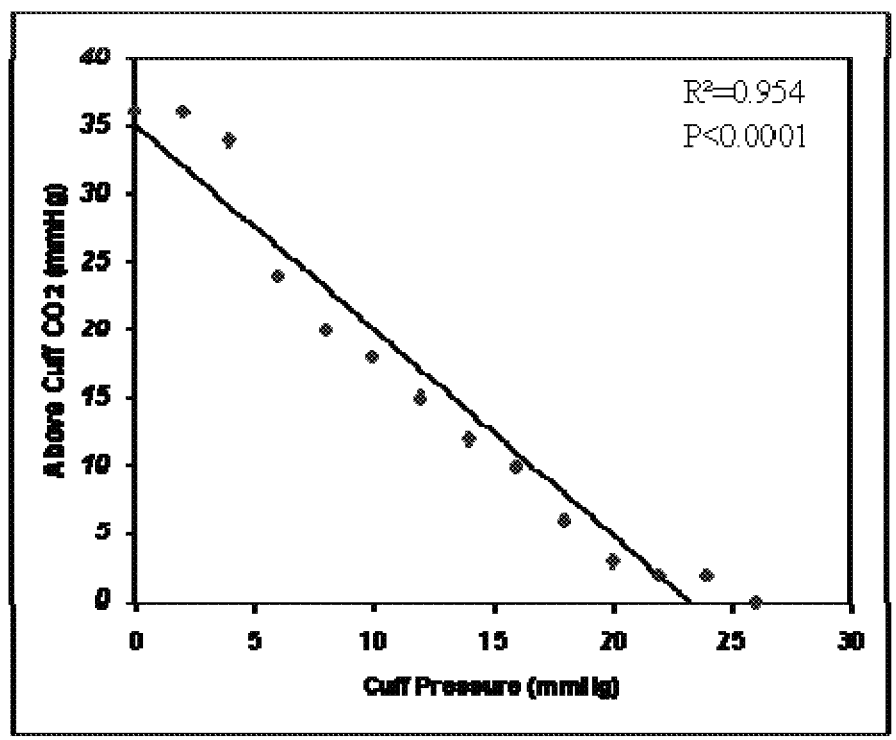
FIG. 12 shows the correlation between endotracheal tube cuff pressures and $CO_2$ levels measured between the cuff and the vocal cords, during an experiment performed according to the teaching of the present invention.

FIG. 12 shows the correlation between endotracheal tube cuff pressures and $CO_2$ levels measured between the cuff and the vocal cords. At an endotracheal tube cuff pressure of 26 mm Hg or higher, no $PCO_2$ was recorded at all 3 anatomic locations. At an endotracheal tube cuff pressure of 25 mm Hg, $PCO_2$ was detected only between the cuff and the vocal cords. Once the endotracheal tube cuff pressure reached 24 mm Hg $CO_2$ leakage was measured at all locations. At all levels of cuff pressures the maximal difference in $PCO_2$ readings between the various anatomic locations was less than 2 mm Hg.

Phase 2—Porcine Model

Figure 13A:
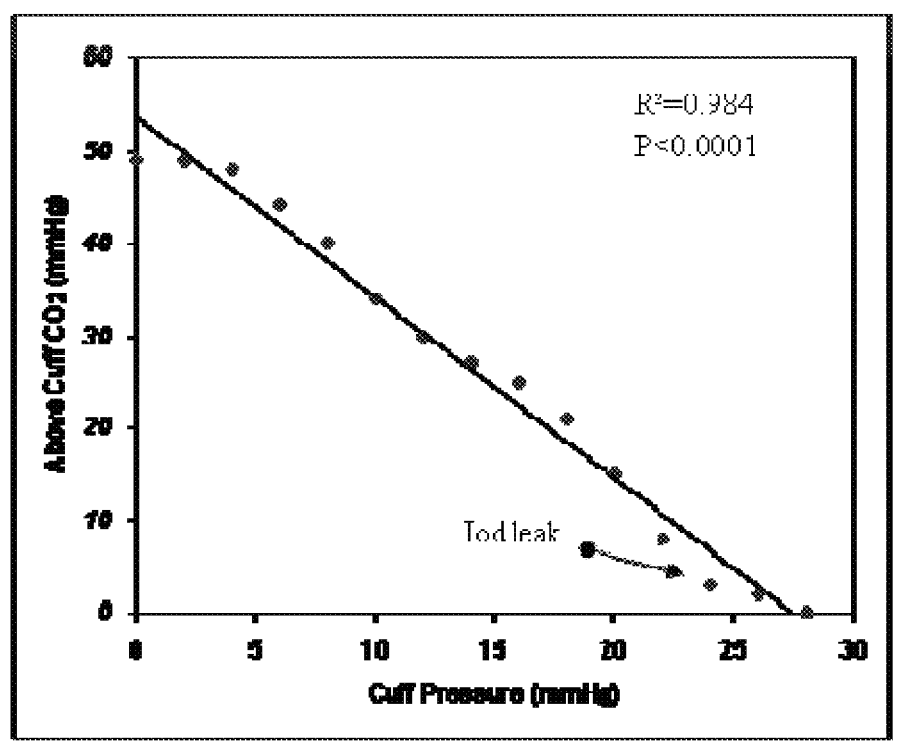
FIGS. 13a-b show correlation between endotracheal tube cuff pressure and upper airway CO2 levels in two porcine models.
Figure 13B:
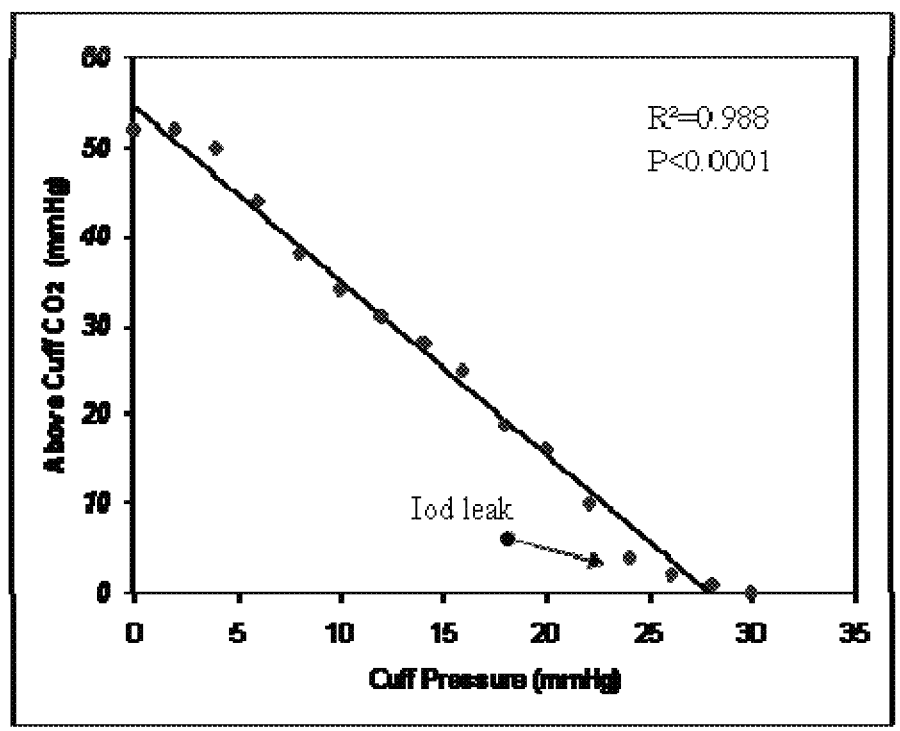

FIGS. 13a-b show correlation between endotracheal tube cuff pressure and upper airway $CO_2$ levels in the two porcine models. The black arrow marks the point at which iodine solution leakage was first detected.

In animal "A" (FIG. 13a) the minimal cuff pressure needed to prevent $CO_2$ leakage was 28 mm Hg while the minimal cuff pressure needed to prevent iodine solution leakage around the cuff was 24 mm Hg, a pressure at which a $PCO_2$ leakage of 2-3 mm Hg was already measured. There was a linear correlation between endotracheal cuff pressure and $PCO_2$ leakage above the cuff ($R^2$=0.984, p<0.0001).

In animal "B" (FIG. 13b) the minimal cuff pressure needed to prevent $CO_2$ leakage around the endotracheal cuff was 30 mm Hg while the minimal cuff pressure needed to prevent iodine solution leakage around the cuff was 25 mm Hg, a pressure at which a $PCO_2$ leakage of 3-4 mm Hg was measured. There was a linear correlation between the endotracheal tube cuff pressure and $PCO_2$ leakage above the cuff ($R^2$=0.988, p<0.0001).

Phase 3—Human Subjects

Baseline characteristics of the patients are summarized in Table 1, below.

TABLE 1

| | N = 60 |
|---|---|
| Age (years) | 58.5 ± 16.2* |
| Sex (male/female) | 44/16 |
| Weight (kg) | 79.4 ± 14.9* |
| Height (cm) | 168.9 ± 10.1* |
| Patients with mild obstructive lung disease | 6 (10%)† |
| Patients with mild restrictive lung disease | 1 (2%)† |
| Tube size: | |
| 7.5 (mm ID) | 20 (33%)† |
| 8 (mm ID) | 16 (27%)† |
| 8.5 (mm ID) | 24 (40%)† |
| Peak inspiratory pressure (mm Hg) | 21.2 ± 0.6* |
| End-tidal $CO_2$ (mm Hg) | 35.3 ± 2.4* |

TABLE 1-continued

| | N = 60 |
|---|---|
| Type of operation | |
| Abdominal laparoscopic surgery | 4 (7%)† |
| Open abdominal surgery | 22 (37%)† |
| Orthopedic | 22 (37%)† |
| Urological | 2 (3%)† |
| Other | 10 (17%)† |

*Data are expressed as means ± standard deviations.
†Data are expressed as numbers of patients (percentage in parentheses).

The mean age of the patients was 58.5±16.2 years. The mean peak inspiratory pressure was 21.2±0.6 mm Hg. Although patients with severe pulmonary diseases were excluded from the study ($FEV_1$ or VC less than 50% of predicted), six patients (10%) had mild obstructive lung disease and one patient had mild restrictive lung disease.

The results from the human simulator and the porcine model, demonstrated a linear correlation between $PCO_2$ leakage measurements and endotracheal tube cuff pressures. A $PCO_2$ leakage measurement was considered clinically significant if it was higher than 2 mm Hg proximal to the endotracheal tube cuff via the external mini-guide lumen of the Hi-Lo® Evac ETT. This was due to the fact that iodine solution leakage occurred only when the $PCO_2$ leakage readings were higher than 2 mm Hg.

Figure 14:
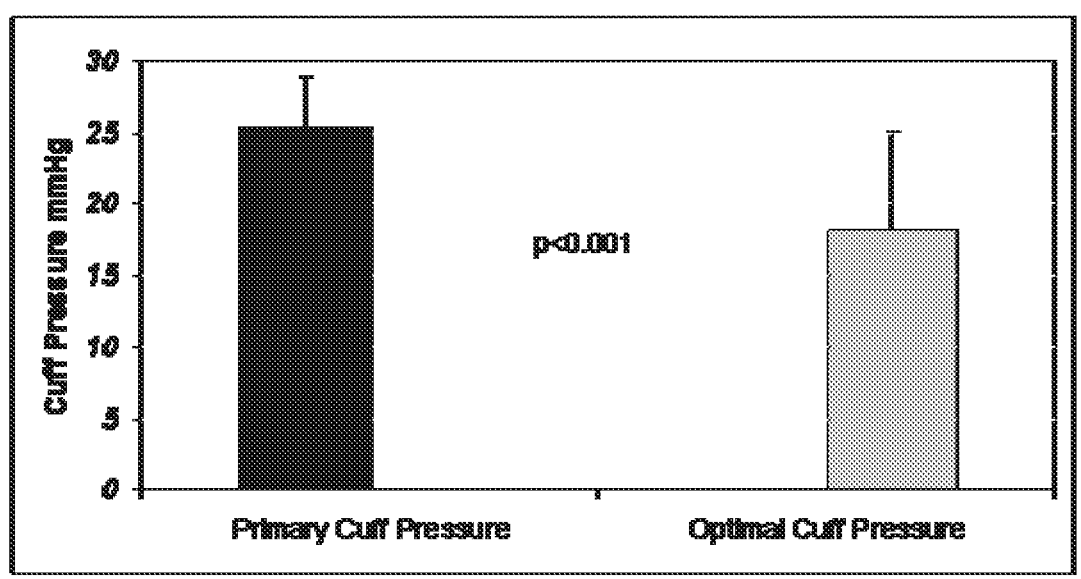
FIG. 14 shows comparison between the initial mean endotracheal tube cuff pressure, determined clinically by a anesthesiologist using the audible leakage test and exhalation-inhalation volume difference, to the mean optimal cuff pressure determined by CO2 leakage monitoring (n=60)

FIG. 14 shows comparison between the initial mean endotracheal tube cuff pressure, determined clinically by the anesthesiologist using the audible leakage test and exhalation-inhalation volume difference, to the mean optimal cuff pressure determined by CO2 leakage monitoring. The mean initial endotracheal tube cuff pressure of all of the study population, determined clinically by the anesthesiologist, was significantly higher than the mean optimal cuff pressure determined by upper airway $PCO_2$ leakage monitoring proximal to the endotracheal tube cuff, 25.2±3.6 vs. 18.2±7.8 mm Hg respectively, p<0.001.

Figure 15:
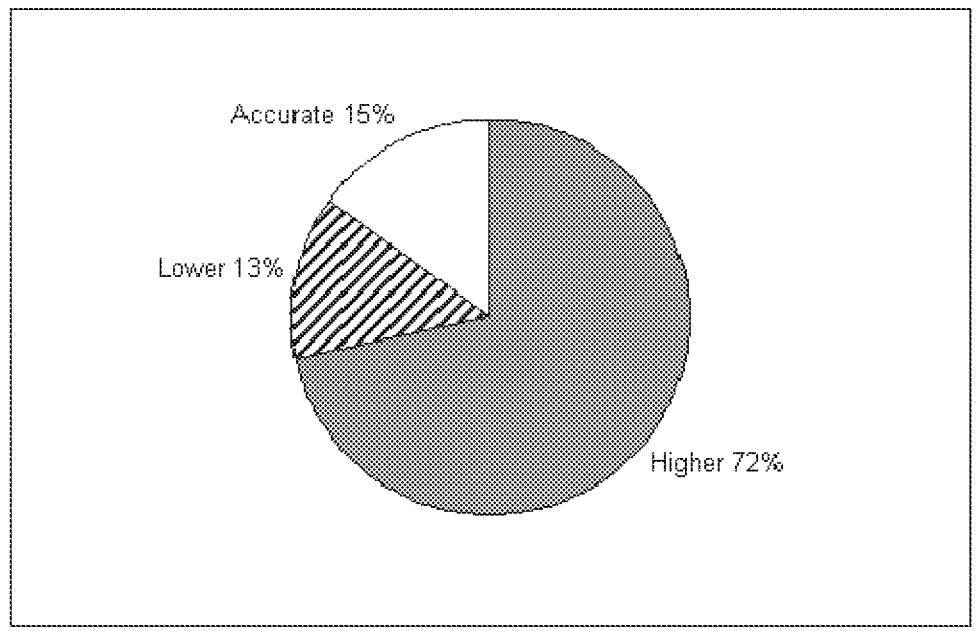
FIG. 15 shows percentage of patients with initial endotracheal tube cuff pressure significantly higher, lower, or accurate compared to the optimal cuff pressure determined by $PCO_2$ leakage monitoring (n=60).

FIG. 15 shows percentage of patients with initial endotracheal tube cuff pressure significantly higher, lower, or accurate compared to the optimal cuff pressure determined by $PCO_2$ leakage monitoring (n=60).

In 43 patients (72%) the clinically determined endotracheal tube cuff pressure was significantly higher than the optimal cuff pressure determined by $CO_2$ leak, with a mean change of 10.2 mm Hg in cuff pressure, 25.4±3.9 vs. 15.2±4.7 mm Hg, p<0.0001.

In 8 patients (13%) the initial endotracheal tube cuff pressures were significantly lower than the optimal cuff pressure. Nine patients (15%) had an initial endotracheal tube cuff pressure similar to the optimal cuff pressure.

In 3 patients $CO_2$ leakage continued despite were exceptionally high cuff pressure, up to 35 mm Hg. The pressures determined by the anesthesiologist in these patients were 30, 32 and 33 mm Hg. After distal repositioning of the endotracheal tube the cuff pressures needed to prevent $CO_2$ leakage were reduced to less than 30 mm Hg similar to the rest of the study population. Since cuff pressures required for complete sealing were reduced dramatically after distal reposition, it was assumed that the primary incomplete sealing, was probably due to a very high proximal airway position causing mal contact between the endotracheal tube cuff and the patient airway anatomy (e.g., direct contact between the cuff and the vocal cords).

During surgery a new leakage of $CO_2$ around the endotracheal tube cuff developed in 16 patients (27%) attributable to variable causes such as increased peak inspiratory pressure by more than 5 mm Hg due to laparoscopic surgery with abdominal gas inflation, light anesthesia or inadequate neuromuscular blockade, change of head position due to surgical requirements and ETT movement during surgery.

Table 2, below summarizes the causes of a "new" leakage during operation.

TABLE 2

| Increase in peak inspiratory pressure | 10/11 |
|---|---|
| Gas inflation of the abdomen | 4/4 |
| Inadequate neuromuscular block | 3/4 |
| Light anesthesia | 3/3 |
| Change of patients' head position | 5/9 |
| Change of tube position | 1/2 |

During surgery $CO_2$ recordings were obtained at all 3 anatomical locations and differences in $PCO_2$ readings were less than 2 mm Hg. After a mean of 9±4 measurements through the suction mini-guide catheter attached to the endotracheal tube, no further readings could be obtained due to obstruction by secretions so further $PCO_2$ readings were obtained only from the plastic airway (hypopharynx) and from the nares.

DISCUSSION

Methods used today to determine adequate cuff filling are either inaccurate or cumbersome [Petring O U, Adelhoj B, Jensen B N, et al. Prevention of silent aspiration due to leaks around cuffs of endotracheal tubes. Anesth Analg 1986; 65:777-780; Young P J, Basson C, Hamilton D, Ridley S A. Prevention of tracheal aspiration using the pressure-limited tracheal tube cuff. Anaesthesia 1999; 54: 559-563].

In this study the determining of the appropriate endotracheal tube cuff filling was performed by continuous $CO_2$ pressure ($PCO_2$) monitoring at the upper airway, in accordance with the teachings of the present invention. The linear correlation found between the endotracheal tube cuff pressure and $CO_2$ leakage above the cuff shows that $PCO_2$ can be used as a quantitative indicator of air leak. Although there was an overall linear correlation between endotracheal tube cuff pressure and $PCO_2$ in the upper airways ($R^2$>0.91, p<0.0001 for all 3 anatomical locations), the correlation seems less linear at the beginning and at the end of the curve with lower $PCO_2$ changes than expected compared to the increase in cuff pressure. The observed non-linearity can be explained by the wide dynamic range (0-40 mm Hg) and relatively low sensitivity (±1 mm Hg) of the capnograph. This non-linearity can be avoided or reduced using a capnograph having a lower dynamic range (e.g., 0-10 mm Hg) and a higher sensitivity (e.g., 0-1 mm Hg).

The rational for this observation can be that at the very low cuff pressures there is still a considerable volume allowing continuous $CO_2$ leak, and at the high cuff pressures, with minimal $CO_2$ leak, there is a need for higher changes in cuff pressures in order to achieve complete sealing of the trachea by the cuff.

In phase 2 of the present study a porcine model was used assessing iodine leakage around the cuff. As iodine is less viscous than pharyngeal secretions it was assumed that the cuff pressure needed to prevent iodine leakage is sufficient to prevent secretion leakage around the endotracheal tube cuff. In this model, using sequential increases of 2 mm Hg in cuff pressure, iodine leakage occurred only when $PCO_2$ readings were higher than 2 mm Hg, suggesting that $PCO_2$ leakage test has a safety margin of 2 mm Hg. Based on these findings and considering that maximal change in $PCO_2$ measurements between the 3 locations was less than 2 mm Hg, it was concluded that for clinical practice measurements of $PCO_2$ at the oropharynx or the nostrils are equivalent to distal measurements just above cuff. The second phase of the study was conducted in only two pigs due to limitations and restrictions by the National Institute of Health Guidelines for the Care and Use of Laboratory Animals. Differences between the cuff pressure needed to prevent $CO_2$ leakage and that needed to prevent iodine leakage in both pigs were almost identical and it seemed inappropriate to sacrifice more animals for this model.

In the third phase of the study the method was evaluated in patients undergoing elective surgery under general anesthesia. The mean initial endotracheal tube cuff pressure determined clinically by the anesthesiologist was significantly higher than the optimal cuff pressure assessed by $CO_2$ leakage monitoring. In all patients, 25.2±3.6 vs. 18.2±7.8 mm Hg, p<0.001; in 72% of the patients, primary endotracheal tube cuff pressures were significantly higher than the optimal cuff pressure determined by $PCO_2$ readings, with a mean change of 10.2 mm Hg.

Although the general tendency of the anesthesiologists was to "overshoot" the initial cuff pressure, in 13% of the cases lower than optimal initial cuff pressures was found. Moreover, during surgery, a "new" leakage developed in 27% of the patients, potentially exposing them to aspiration risk. This variability in cuff pressure, observed even in stable elective surgery patients, emphasizes the need for an accurate, continuous bedside method to determine the appropriate cuff pressure.

An important problem encountered during the study was obstruction by secretions of the mini-guide lumen of the Hi-Lo® Evac ETT after several aspirations for $PCO_2$ measurements despite suctioning of the upper airways. In contrast, $PCO_2$ readings through nasal cannula or from the oropharynx through the plastic airway were easily obtained after secretion clearance by oral suctioning.

Another important issue regards the position of the endotracheal tube. Malpositioned endotracheal tube is hazardous for intubated patients. Insertion of an endotracheal tube too distally leads to endobronchial intubation, which may cause collapse of the contralateral lung, while proximal insertion may lead to accidental extubation or vocal cord trauma [Streitz J M Jr, Shapshay S M. Airway injury after tracheotomy and endotracheal intubation. Surg Clin North Am 1991; 71:1211-1230]. Several formulae and other methods have been proposed to estimate the optimal length for endotracheal tube insertion [Owen R L, Cheney F W. Endobronchial intubation: a preventable complication. Anesthesiology 1987; 67:255-257; Mehta S. Intubation guide marks for correct tube placement. A clinical study. Anaesthesia 199; 46:306-308; Patel N, Mahajan R P, Ellis F R. Estimation of the correct length of tracheal tubes in adults Anaesthesia. 1993; 48:74-75; Cherng C H, Wong C S, Hsu C H, Ho S T. Airway length in adults: estimation of the optimal endotracheal tube length for orotracheal intubation. J Clin Anesth. 2002; 14:271-274]. However, none is always satisfactory.

In the current study, 3 patients had a $CO_2$ leakage despite exceptionally high (>35 mm Hg) cuff pressures. However, pressure decreased to less than 30 mm Hg (as has been in the rest of the study population) after distal repositioning of the endotracheal tube. Although it was not the aim of the study, continuously $CO_2$ leakage near an appropriately inflated cuff can be used as a marker for malpositioned endotracheal tube. Incessant $CO_2$ leakage around the endotracheal tube cuff can occur when there is incomplete sealing due to mal contact with the vocal cords, endobronchial intubation ($CO_2$ from the contralateral lung) or above vocal cord intubation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An alerting and controlling system, the system comprising:
    a measuring device connectable to an endotracheal tube associated with a cuff inflatable below the vocal cords of a subject, for measuring a level of at least one measure being indicative of the presence of leakage of secretions from above said cuff to the lungs of the subject; and
    a controller having a circuit, said circuit being configured for: (i) adjusting inflation of said cuff responsively to said level of said at least one measure, and (ii) alerting that said endotracheal tube is malpositioned in the airway of the subject if there is a leakage of secretions and an inflation pressure of said cuff exceeds a predetermined threshold.

2. The system of claim 1, further comprising said endotracheal tube and said cuff.

3. The system of claim 1, wherein said at least one measure comprises carbon dioxide concentration between said cuff and said vocal cords.

4. The system of claim 1, wherein said at least one measure comprises carbon dioxide concentration above said vocal cords.

5. The system of claim 1, wherein said at least one measure comprises carbon dioxide concentration at a nostril of the subject.

6. The system of claim 1, wherein said at least one measure comprises acoustical data being indicative of leakage near said cuff outside said endotracheal tube.

7. The system of claim 1, wherein said at least one measure comprises pressure data being indicative of fluid flow in a leaking duct near said cuff outside said endotracheal tube.

8. The system of claim 1, wherein said at least one measure comprises flow data being indicative of fluid flow in a leaking duct near said cuff outside said endotracheal tube.

9. The system of claim 1, wherein said at least one measure comprises optical data being indicative of presence of secretions near said cuff outside said endotracheal tube.

10. The system of claim 1, wherein said at least one measure comprises electrical characteristics of fluid above said cuff outside said endotracheal tube.

11. The system of claim 1, further comprising an additive delivering device configured for delivering at least one identifiable additive through said endotracheal tube, wherein said at least one measure comprises presence or concentration of said at least one identifiable additive.

12. The system of claim 11, wherein said at least one identifiable additive is characterized by measurable electric properties.

13. The system of claim 11, wherein said at least one identifiable additive is characterized by measurable magnetic properties.

14. The system of claim 11, wherein said at least one identifiable additive is characterized by measurable optical properties.

15. The system of claim 11, wherein said at least one identifiable additive is characterized by measurable radiation properties.

16. The system of claim 11, wherein said at least one identifiable additive is characterized by measurable fluorescent properties.

17. The system of claim 11, wherein said at least one identifiable additive comprises at least one inert gas.

18. The system of claim 11, wherein said at least one identifiable additive comprises at least one colored gas.

19. The system of claim 11, wherein said at least one identifiable additive comprises at least one radioisotope.

20. The system of claim 1, wherein said controller is configured for alerting when said leakage is detected.

* * * * *